(12) United States Patent
Suffritti et al.

(10) Patent No.: US 11,571,501 B2
(45) Date of Patent: Feb. 7, 2023

(54) APPARATUS AND METHOD FOR TESTING INTEGRITY OF AN ULTRAFILTER MEMBRANE

(71) Applicant: GAMBRO LUNDIA AB, Lund (SE)

(72) Inventors: Mauro Suffritti, Medolla (IT); Michela Carpani, San Felice Sul Panaro (IT)

(73) Assignee: Gambro Lundia AB, Lund (SE)

( * ) Notice: Subject to any disclaimer, the term of this patent is extended or adjusted under 35 U.S.C. 154(b) by 154 days.

(21) Appl. No.: 17/050,050

(22) PCT Filed: Apr. 19, 2019

(86) PCT No.: PCT/EP2019/060246
§ 371 (c)(1),
(2) Date: Oct. 23, 2020

(87) PCT Pub. No.: WO2019/206837
PCT Pub. Date: Oct. 31, 2019

(65) Prior Publication Data
US 2021/0093771 A1 Apr. 1, 2021

(30) Foreign Application Priority Data

Apr. 25, 2018 (EP) .................................. 18169176

(51) Int. Cl.
*A61M 1/34* (2006.01)
*B01D 61/14* (2006.01)
(Continued)

(52) U.S. Cl.
CPC ......... *A61M 1/3417* (2014.02); *B01D 61/145* (2013.01); *B01D 61/18* (2013.01);
(Continued)

(58) Field of Classification Search
CPC ........ A61M 1/3417; A61M 2205/3331; A61M 2205/52; A61M 2205/70;
(Continued)

(56) References Cited

U.S. PATENT DOCUMENTS

| 4,614,109 A | 9/1986 | Hofmann |
| 4,702,829 A | 10/1987 | Hajime |

(Continued)

FOREIGN PATENT DOCUMENTS

| CN | 101341389 A | 1/2009 |
| CN | 101622531 A | 1/2010 |

(Continued)

OTHER PUBLICATIONS

1st Chinese Office Action issued by the CNPTO for corresponding Chinese Patent Application No. 2019800284856, Office Action dated Mar. 15, 2022—7 Pages.

(Continued)

*Primary Examiner* — Pranav N Patel
(74) *Attorney, Agent, or Firm* — K&L Gates LLP

(57) ABSTRACT

An apparatus for extracorporeal treatment of blood (1) has a supply line (2), a waste line (13) and an ultrafilter (19; 70) inserted in the supply line (2). An air inlet line is connected to the first chamber (21; 72) of the ultrafilter (19; 70) and a pressure sensor (41) configured for detecting pressure in the waste line (13). A controller (50) is configured to carry out, with the hydraulic circuit (100) in by-pass configuration, an integrity test procedure for detecting if the ultrafilter membrane has multiple or single fiber breaks. A method of testing the ultrafilter (19; 70) is also disclosed.

21 Claims, 4 Drawing Sheets

(51) Int. Cl.
  *B01D 61/18* (2006.01)
  *B01D 61/22* (2006.01)
  *B01D 61/24* (2006.01)
  *B01D 65/10* (2006.01)

(52) U.S. Cl.
  CPC .......... *B01D 61/22* (2013.01); *B01D 61/243* (2013.01); *B01D 65/102* (2013.01); *A61M 2205/3331* (2013.01); *A61M 2205/52* (2013.01); *A61M 2205/70* (2013.01); *B01D 2311/14* (2013.01); *B01D 2311/22* (2013.01); *B01D 2313/083* (2013.01); *B01D 2313/18* (2013.01); *B01D 2313/243* (2013.01); *B01D 2317/02* (2013.01)

(58) Field of Classification Search
  CPC .......... A61M 2205/705; A61M 1/1672; B01D 61/145; B01D 61/18; B01D 61/22; B01D 61/243; B01D 65/102; B01D 2311/14; B01D 2311/22; B01D 2313/083; B01D 2313/18; B01D 2313/243; B01D 2317/02; B01D 2317/025; B01D 65/104; B01D 61/58
  See application file for complete search history.

(56) References Cited

U.S. PATENT DOCUMENTS

| | | |
|---|---|---|
| 4,834,888 A | 5/1989 | Polaschegg |
| 5,064,529 A | 11/1991 | Hirayama |
| 5,282,380 A | 2/1994 | Dileo et al. |
| 5,594,161 A | 1/1997 | Randhahn |
| 5,674,404 A | 10/1997 | Kenley |
| 5,808,181 A | 9/1998 | Wamsiedler et al. |
| 6,066,261 A | 5/2000 | Moeko |
| 6,187,207 B1 | 2/2001 | Brauer |
| 6,228,271 B1 | 5/2001 | Cote |
| 6,280,632 B1 * | 8/2001 | Polaschegg ......... A61M 1/1672 210/103 |
| 8,486,272 B2 | 7/2013 | Rauch |
| 8,518,258 B2 | 8/2013 | Balschat et al. |
| 2003/0010719 A1 | 1/2003 | Brugger |
| 2004/0019438 A1 | 1/2004 | Padgett |
| 2004/0079703 A1 | 4/2004 | Chevallet |
| 2005/0011833 A1 | 1/2005 | Stahl |
| 2005/0126998 A1 | 6/2005 | Childers |
| 2006/0113226 A1 | 6/2006 | Breitner |
| 2011/0138936 A1 | 6/2011 | Collins et al. |
| 2012/0175296 A1 | 7/2012 | Wehmeyer |
| 2012/0199526 A1 | 8/2012 | Kopperschmidt |
| 2013/0055792 A1 | 3/2013 | Scheu |
| 2013/0327691 A1 | 12/2013 | Burbank |
| 2017/0138833 A1 | 5/2017 | Burkert |

FOREIGN PATENT DOCUMENTS

| | | |
|---|---|---|
| DE | 4239937 A1 | 6/1994 |
| EP | 0407737 B1 | 8/1993 |
| EP | 0491981 B1 | 2/1995 |
| EP | 0951303 A1 | 10/1999 |
| EP | 0960624 A1 | 12/1999 |
| EP | 0925796 B1 | 3/2004 |
| EP | 1194217 B1 | 6/2004 |
| EP | 1898973 B1 | 5/2010 |
| EP | 2418012 A1 | 2/2012 |
| EP | 2550984 A1 | 1/2013 |
| EP | 2567750 A1 | 3/2013 |
| EP | 1119404 B2 | 5/2013 |
| EP | 1897605 B1 | 4/2014 |
| EP | 3037156 A1 | 6/2016 |
| WO | WO 9745193 A1 | 12/1997 |
| WO | WO2007003980 * | 1/2007 |
| WO | WO 2010027437 A2 | 3/2010 |
| WO | WO 2010027437 A3 | 4/2010 |
| WO | WO 2012124425 | 9/2012 |
| WO | WO 2016193941 | 12/2016 |

OTHER PUBLICATIONS

Chinese Search Report issued by the CNPTO for corresponding Chinese Patent Application No. 2019800284856, Search Report dated Mar. 8, 2022—3 Pages.
Extended European search report; Corresponding European Application No. 18169176.7; report dated Oct. 19, 2018 (Oct. 19, 2018). 7 Pages.
International Search Report and Written Opinion of the International Searching Authority; corresponding PCT Application No. PCT/EP2019/060246; report dated Jul. 1, 2019 (Nov. 7, 2019). 13 Pages.

* cited by examiner

APPARATUS AND METHOD FOR TESTING INTEGRITY OF AN ULTRAFILTER MEMBRANE

PRIORITY CLAIM

The present application is a National Phase of International Application No. PCT/EP2019/060246, filed Apr. 19, 2019, which claims priority to EP Application No. 18169176.7, filed Apr. 25, 2018. The entire contents of each application are incorporated herein by reference and relied upon.

DESCRIPTION

The invention relates to an apparatus and to a method for testing the integrity of the semipermeable membrane of one or more ultrafilters. The invention may apply for testing the membrane integrity of one or more ultrafilters in apparatus for extracorporeal blood treatment. For example, the hydraulic circuit of apparatus for hemodialysis, or hemofiltration, or hemodiafiltration may include one or more ultrafilters configured for removing germs and other undesired particles which may be present in the dialysis liquid and/or in the replacement liquid prepared by the apparatus. As ultrafilters are typically used for a number of treatments, the ultrafilters membrane integrity needs to be periodically verified in order to guarantee the membrane ability to purify liquid.

Various methods have been used in the past to check the integrity of an ultrafilter membrane. In particular, the testing methods used in more recent years have strived to be reliable in the detection of ruptures of the membrane, without requiring excessive complication on the apparatus and using as possible components already present in conventional extracorporeal blood treatment apparatus.

For example, EP 1897605 B1 relates to a method and apparatus for testing integrity of an ultrafilter membrane wherein gas is fed into a chamber of the tested ultrafilter via a feed line. Gas is put under pressure by a given amount of liquid also fed through the same feed line. Then, a measure of liquid flow is made to detect leakage through the ultrafilter membrane.

WO 2012124425 A1 relates to a hemodialysis apparatus wherein the control system is configured for executing a method of testing the integrity of an ultrafilter membrane by filling a part of the hydraulic circuit with air, creating a negative pressure in the water filled part of the hydraulic circuit, and monitoring the negative pressure thus created.

In particular, the control system operates the dialysis pump to create a first negative pressure on the liquid side of the tested ultrafilter, then stops the dialysis pump and operates an ultrafiltration pump to create a second and more negative pressure. The control system then verifies that the second more negative pressure remains substantially stable. If this does not happen a defective membrane is identified.

EP1898973 B1 relates to an apparatus for the testing of filters aiming to avoid use of high pressures in the hydraulic circuit connected to the ultrafilter. In particular, this document shows a method of testing ultrafilters comprising generating an overpressure on one side of the ultrafilter membrane and a negative pressure on the opposite side thereof.

Although the above methods have been used in the past, the Applicant considered that the state of the art may still be improved.

An aim of the invention is to provide a method and an apparatus for testing ultrafilters, which improves test rapidity without compromising test reliability.

A further aim of the invention is to offer a method and an apparatus suitable for testing ultrafilters of apparatus for extracorporeal blood treatment, such as hemodialysis, hemofiltration or hemodiafiltration apparatus.

An additional aim of the present invention is to make available a precise and sensitive method and apparatus for testing ultrafilters which is able to distinguish over different types of ultrafilter membrane integrity problems.

SUMMARY

At least one of the above objects is substantially reached by an apparatus according to one or more of the appended apparatus claims.

At least one of the above objects is substantially reached by a method according to one or more of the appended method claims.

Apparatus and methods according to aspects of the invention and capable of achieving one or more of the above objects are here below described.

A 1st aspect concerns an extracorporeal blood treatment apparatus (1) comprising:
  a supply line (2) having an inlet end connectable to a source of treatment liquid and an outlet end connectable to an inlet port of a blood treatment device (5);
  a waste line (13) having an inlet end connectable to an outlet port the blood treatment device (5) and an outlet end connectable to a discharge of used treatment liquid, wherein the supply line (2) and the waste line (13) are part of an hydraulic circuit (100);
  an ultrafilter (19) inserted in the supply line (2) and having a semipermeable membrane dividing the ultrafilter (19) into a first chamber (21) and a second chamber (22), the ultrafilter (19) presenting:
    a first port connecting a first tract (24) of the supply line (2) to the first chamber (21),
    a second port connecting the second chamber (22) to a second tract (26) of the supply line (2);
  an air inlet line (30) connected to the first chamber (21) of the ultrafilter (19) or to the first tract (24) of the supply line (2);
  at least one waste pump (34, 38) on the waste line (13);
  at least one pressure sensor (41) configured for detecting pressure in one of:
    the second chamber (22) of the ultrafilter (19),
    the second tract (26) of the supply line (2),
    the waste line (13);
  a controller (50) connected to the waste pump (34, 38) and the at least one pressure sensor (41) and configured to carry out an integrity test procedure comprising the following steps:
    causing filling of the first chamber (21) of the ultrafilter (19) with air,
    after filling the first chamber (21) with air, increasing a negative pressure or creating a negative pressure (i.e. either making more negative the pressure relative to atmospheric pressure present in the ambient where the apparatus (1) is installed or creating a pressure negative relative to said atmospheric pressure present in the ambient where the apparatus (1) is installed) in the second chamber (22) of the ultrafilter (19) by operating the waste pump (34, 38), verifying, while the waste pump (34, 38) is running, if the pressure sensed by the at least one pressure sensor (41) reaches a set negative pressure threshold (Pt), determining that the ultrafilter (19) semipermeable membrane has a multi-fiber break if pressure sensed by the at least one pressure sensor (41) during said verification step reaches said set negative pressure threshold (Pt) within a set time interval (T).

For example the air inlet line may include at least one of an air valve and an air pump connected to the controller (50); the step of causing filling of the first chamber of the ultrafilter comprises execution by the controller (50) of at least one of commanding opening of the air valve and commanding operation of the air pump.

In a 2nd aspect according to the 1st aspect the hydraulic circuit is configurable according to a by-pass configuration, where the supply line (2) is in fluid communication with the waste line (13) via a bypass line bypassing the blood treatment device (5) and directly connecting the outlet end of the supply line (2) and the inlet end of the waste line (13), and according to a normal configuration, where the outlet end of the supply line (2) communicates with the inlet end of the waste line (13) through the blood treatment device (5).

In a 3rd aspect according to the 2nd aspect the controller (50) is configured to carry out said integrity test procedure comprising with the hydraulic circuit (100) in by-pass configuration.

In a 4th aspect according to any one of the preceding aspects said integrity test procedure, which the controller (50) is configured to execute, comprises operating the waste pump (34, 38) in closed-loop as follows:

during said step of filling the first chamber (21) of the ultrafilter (19) with air, achieved by at least opening an air valve or operating an air pump operative on the air inlet line (30), also operating the waste pump (34, 38) based on a first set negative pressure value (P1) which is a desired set value to be reached by pressure sensed by the at least one pressure sensor (41), after said step of filling the first chamber (21) of the ultrafilter (19) with air, once the first chamber (21) has been emptied from liquid and filled with air, operating the waste pump (34, 38) based on a second set negative pressure value (P2), different from the first set value (P1) and which represents a second desired set value to be reached by pressure sensed by the at least one pressure sensor (41).

In a 5th aspect according to the 4th aspect, the second set negative pressure value (P2) is more negative than the first pressure value.

In a 6th aspect according to the 4th or the 5th aspect the set negative pressure threshold (Pt), which is checked during said verifying step, has a negative value intermediate between said first set pressure value (P1) and said second set pressure value (P2).

In a 7th aspect according to any one of the preceding three aspects the first set pressure value (P1) is selected in a pressure range between −150 and −450 mm Hg mmHg.

In an 8th aspect according to any one of the preceding four aspects, the second set pressure value (P2) is selected in a pressure range between −300 and −700 mm Hg mmHg.

In 9th aspect according to any one of the preceding five aspects the second pressure value is at least 100 mm Hg mmHg more negative than the first set pressure value.

In a 10th aspect according to any one of the preceding aspects the extracorporeal blood treatment apparatus (1) comprises a fresh fluid pump positioned on:

the air inlet line (30), or the first tract (24) of the supply line (2), between the air injection point and the first port of the ultrafilter (19).

In an 11th aspect according to the preceding aspect the controller (50) is also connected to the fresh fluid pump and configured to operate the fresh fluid pump during said step of filling the first chamber (21) of the ultrafilter (19) with air.

In a 12th aspect according to the preceding aspect wherein the controller is configured to open the air valve (31) with a delay from start of operation of the fresh fluid pump.

In a 13th aspect according to any one of the preceding three aspects, wherein the apparatus (1) comprises a safety pressure sensor (90) located between fresh fluid pump (32) and the first chamber of the ultrafilter (19), wherein the controller (50) is configured to stop operation of fresh fluid pump (32) if a pressure difference or pressure ratio between pressure detected by pressure sensor (41) and pressure detected by safety pressure sensor (90) exceeds an identified safety threshold.

In a 14th aspect according to any one of the preceding aspects, wherein the integrity test procedure comprises the following further steps which the controller (50) is configured to execute:

hydraulically isolating the ultrafilter (19);

receiving pressure values detected by the at least one pressure sensor (41) at the end of a given transitory period after having hydraulically isolated the ultrafilter (19);

verifying if two stability conditions are met:

pressure values detected by the at least one pressure sensor (41) at the end of the transitory period are below an auxiliary negative pressure threshold (Pt2), and a variation by unit of time (dP/dt) of said pressure values detected by the at least one pressure sensor (41) at the end of the transitory period is below a set pressure differential (ΔP), determining that the semipermeable membrane of the ultrafilter (19) has a multi-fiber break if said two stability conditions are not both met.

The further steps described above may be executed by the controller after the steps of the preceding aspects.

In a 15th aspect according to the preceding aspect the auxiliary negative pressure threshold (Pt2) is −350 mmHg.

In a 16th aspect according to any one of the preceding two aspects the set pressure differential (ΔP) is 4 mmHg/s.

In a 17th aspect according to any one of the preceding three aspects the auxiliary negative pressure threshold (Pt2) is less negative than the pressure threshold (Pt).

In an 18th aspect according to any one of the preceding four aspects the controller (50) is configured to determine said variation by unit of time (dP/dt) assigning a respective weight to each received pressure value, with the pressure values received during an initial phase of detection having more weight than pressure values received during an ending phase of detection.

In a 19th aspect according to any one of the preceding aspects the integrity test procedure comprises the following further steps which the controller (50) is configured to execute:

hydraulically isolating the ultrafilter (19);

receiving pressure values detected by the at least one pressure sensor (41) during a further test interval after a/said transitory period following hydraulic isolation of the ultrafilter (19), verifying if a variation by unit of time (dP/dt) of said pressure values detected by the at least one pressure sensor (41) during the further test interval remains below a further set pressure differential (Δp2) for at least a portion of said test interval, determining that the semipermeable membrane of the ultrafilter (19) has a single-fiber break if the above last verifying step is not positively passed.

The further steps described above may be executed by the controller after the steps of the preceding aspects.

In a 20th aspect according to the preceding aspect the step of verifying if a variation by unit of time (dP/dt) of said pressure values detected by the at least one pressure sensor (41) during the further test interval remains below a further set pressure differential (Δp2) for at least a portion of said test interval comprises verifying if the variation by unit of time (dP/dt) of said pressure values detected by the at least one pressure sensor (41) during the further test interval remains below 2 mmHg/s for 4 seconds in the first 10 seconds of the further test interval.

In a 21st aspect according to any one of the preceding two aspects,
said further set pressure differential (Δp2) is a fraction of said set pressure differential (ΔP).

In a 22nd aspect according to any one of the preceding three aspects,
said further set pressure differential (Δp2) is less than 70% of said set pressure differential (ΔP).

In a 23rd aspect according to any one of the preceding four aspects,
said further set pressure differential (Δp2) is less than or equal to 50% of said set pressure differential (ΔP).

In a 24th aspect according to any one of the preceding five aspects, the apparatus (1) further comprises:
at least one inlet valve (39) on the supply line (2) to selectively open and close supply of liquid from the source of treatment liquid;
at least one outlet valve (40) on the waste line (13) to selectively open and close flow of used treatment liquid to the discharge;
a flush line (28) connecting a third port of the first chamber (21) of the ultrafilter (19) to the waste line (13), and
at least one flush valve (29) positioned on the flush line to selectively open and close the first chamber (21) of the ultrafilter (19) to the waste line (13).

In a 25th aspect according to the preceding aspect the step of hydraulically isolating the ultrafilter (19) comprises the following sub-steps which the controller (50) is configured to execute:
closing at least said inlet valve, outlet valve, flush valve and optionally the air inlet valve,
stopping the waste pump (34, 38).

In a 26th aspect according to the preceding aspect wherein step of hydraulically isolating the ultrafilter (19) comprises also stopping the fresh fluid pump (32).

In a 27th aspect according to any one of the preceding aspects the apparatus also comprises an auxiliary ultrafilter (70) inserted in the second tract (26) of the supply line (2) and having a semipermeable membrane dividing the auxiliary ultrafilter (70) into a respective first chamber (72) and a respective second chamber (73), the auxiliary ultrafilter (70) presenting:
a first port connecting a first portion (26a) of the second tract (26) of the supply line (2) to the first chamber (72) of the auxiliary ultrafilter (70),
a second port connecting the second chamber (73) of the auxiliary ultrafilter (70) to a second portion (26b) of the second tract (26) of the supply line (2);
an auxiliary air inlet line (76) connected to the first chamber (72) of the auxiliary ultrafilter (70) or to the first portion (26a) of the second tract (26) of the supply line (2);
an auxiliary air valve or an auxiliary air pump (77) on the air inlet line (76).

In a 28th aspect according to the preceding aspect, the at least one pressure sensor (41) is configured for detecting pressure in one of:
the second chamber (73) of the auxiliary ultrafilter (70),
the second portion (26b) of the second tract (26) of the supply line (2),
the waste line (13).

In a 29th aspect according to any one of the preceding two aspects the controller (50) is configured to carry out an auxiliary integrity test procedure comprising the following steps:
causing filling of the first chamber (72) of the auxiliary ultrafilter (70) with air by operating the waste pump (34 and 38); this step may also include execution by the controller (50) of at least one of commanding opening of an auxiliary air valve or operation of an auxiliary air pump (77) operative on the air inlet line (76),
after filling the first chamber (72) of the auxiliary ultrafilter (70) with air, increasing a negative pressure (rendering the pressure more negative relative to atmospheric pressure present in the environment where the apparatus is installed) in the second chamber (73) of the auxiliary ultrafilter (70) by continuing to operate the waste pump (34, 38),
verifying, while the waste pump (34, 38) is running, if the pressure sensed by the at least one pressure sensor (41) reaches a set negative pressure threshold (Pt'),
determining that the auxiliary ultrafilter (70) semipermeable membrane has a multi-fiber break if the pressure sensed by the at least one pressure sensor (41) during said verification step does not reach said set negative pressure threshold (Pt') within an auxiliary set time interval (T').

In a 30th aspect according to the preceding aspect the controller (50) is configured to carry out the auxiliary integrity test procedure with the hydraulic circuit, i.e., the supply line (2) and the waste line (13), in by-pass configuration.

In a 31st aspect according to any one of the preceding two aspects said auxiliary integrity test procedure, which the controller (50) is configured to execute, comprises operating the waste pump (34, 38) in closed-loop as follows:
during said step of filling the first chamber (72) of the auxiliary ultrafilter (70) with air, the controller (50) controls operation of the waste pump (34, 38) based on a first set negative pressure value (P1'), which shall be reached by pressure sensed by the at least one pressure sensor (41),
after said step of filling the first chamber (72) of the auxiliary ultrafilter (70), once the first chamber (72) has been completely emptied from liquid and filled with air, the controller (50) controls operation of the waste pump (34, 38) based on a second set negative pressure value (P2'), which shall be reached by pressure sensed by the at least one pressure sensor (41) and which is different from the first pressure value In a 32nd aspect according to the preceding aspect the set negative pressure threshold (Pt') has a negative value intermediate between said first set pressure value (P1') and said second set pressure value (P2').

In a 33rd aspect according to any one of the preceding two aspects the first set pressure value (P1') is selected in a pressure range between −150 and −450 mm Hg.

In a 34th aspect according to any one of the preceding three aspects the second set pressure value (P2') is selected in the range between −300 and −700 mm Hg mmHg.

In a 35th aspect according to any one of the preceding four aspects the second pressure value (P2') is at least 100 mm Hg mmHg more negative than the first set pressure value (P1').

In a 36th aspect according to any one of the preceding five aspects the set negative pressure threshold (Pt') is selected to have a value which is intermediate between the first and second pressure values (P1', P2').

In a 37th aspect according to any one of the preceding six aspects the controller (50) is configured to check a time related parameter, which is one of:
 a time necessary to reach the first pressure value (P1'),
 a rotation frequency of the waste pump (34, 38),
 a pump rotation period of the waste pump (34, 38),
and to compare this detected time related parameter with a corresponding reference threshold, assigning the identification of a multi-fiber break problem in membrane (20) of ultrafilter (19) if the check on the time related parameter is not passed.

In a 38th aspect according to any one of the preceding nine aspects the auxiliary integrity test procedure comprises the following further steps which the controller (50) is configured to execute:
 hydraulically isolating the auxiliary ultrafilter (70);
 receiving pressure values detected by the at least one pressure sensor (41) at the end of a given transitory period after having hydraulically isolated the auxiliary ultrafilter (70);
 verifying if two stability conditions are met:
  pressure values detected by the at least one pressure sensor (41) at the end of the transitory period are below an auxiliary negative pressure threshold,
  a variation by unit of time (dP/dt) of said pressure values detected by the at least one pressure sensor (41) at the end of the transitory period is below a set pressure differential,
 determining that the semipermeable membrane of the auxiliary ultrafilter (70) has a multi-fiber break if said two stability conditions are not both met.

In a 39th aspect according to the preceding aspect the auxiliary negative pressure threshold is −350 mmHg.

In a 40th aspect according to any one of the preceding two aspects the set pressure differential is 4 mmHg/s.

In a 41st aspect according to any one of the preceding three aspects the variation by unit of time (dP/dt) is determined by assigning a respective weight to each received pressure value, with the pressure values received during an initial phase of detection having more weight than pressure values received during an ending phase of detection.

In a 42nd aspect according to any one of the preceding thirteen aspects the auxiliary integrity test procedure comprises the following further steps which the controller (50) is configured to execute:
 hydraulically isolating the auxiliary ultrafilter (70);
 receiving pressure values detected by the at least one pressure sensor (41) during a further test interval subsequent to the transitory period following hydraulic isolation of the auxiliary ultrafilter (70),
 verifying if a variation by unit of time (dP/dt) of said pressure values detected by the at least one pressure sensor (41) during the further test interval remains below a further set pressure differential (Δp2'), for example below 2 mmHg/s, for at least a portion of said further test interval, for example for 4 s in the first 10 s of the further test interval,
 determining that the semipermeable membrane of the ultrafilter (70) has a single-fiber break if the above last verifying step is not positively passed.

In a 43rd aspect according to the preceding aspect the further set pressure differential (Δp2') is 2 mmHg/s.

In a 44th aspect according to any one of the preceding six aspects the apparatus further includes:
 an auxiliary flush line (86) connecting a third port of the first chamber (72) of the auxiliary ultrafilter (70) to the waste line (13), and
 an auxiliary flush valve (88) positioned on the flush line to selectively open and close the first chamber (72) of the auxiliary ultrafilter (70) to the waste line (13);
wherein the step of hydraulically isolating the auxiliary ultrafilter (70) comprises the following sub-steps which the controller (50) is configured to execute:
 at least closing said inlet valve (39), outlet valve (40), auxiliary flush valve (88), and optionally the air inlet valve and the auxiliary air inlet valve,
 stopping the waste pump (34 and 38) and, when a fresh fluid pump is present also stopping the fresh fluid pump (32).

A 45th aspect concerns a method of testing the integrity of an ultrafilter membrane of an ultrafilter (19; 70), wherein the ultrafilter membrane separates the ultrafilter (19; 70) into a first and a second chamber (21,22; 72, 73).

A 46th aspect concerns a method of testing the integrity of an ultrafilter membrane of at least one ultrafilter (19; 70) of the extracorporeal blood treatment apparatus (1) according to any one of aspects from the 1st to the 44th.

In a 47th aspect according to any one of the preceding two aspects the method comprising executing the following steps:
 emptying the first chamber (21; 72) of the ultrafilter (19; 70) from liquid and filling the first chamber (21; 72) with air,
 after the first chamber (21; 72) has been filled with air, continue extracting liquid from the second chamber (22; 73) of the ultrafilter (19; 70),
 verifying, while extracting liquid from the second chamber (22; 73) of the ultrafilter (19; 70), if the pressure in the ultrafilter (19; 70) second chamber (22; 73) reaches a set negative pressure threshold (Pt, Pt'),
 determining that the ultrafilter (19; 70) semipermeable membrane has a multi-fiber break if the pressure in the second chamber (22; 73) during the step of extracting liquid does not reach (i.e., does not go down enough to reach) said set negative pressure threshold (Pt; Pt') within a set time interval.

In a 48th aspect according to any one of the preceding three aspects the method comprises the following further steps:
 hydraulically isolating the ultrafilter (19; 70);
 waiting a given transitory period;
 verifying if two stability conditions are met:
  values of pressure in the second chamber (22; 73) of the ultrafilter (19; 70) at the end of the transitory period are below an auxiliary negative pressure threshold, for example below −350 mmHg, and
  a variation by unit of time (dP/dt) of said pressure values in the second chamber (22; 73) of the ultrafilter (19; 70) at the end of the transitory period is below a set pressure differential, for example below 4 mmHg/s, determining that the semipermeable membrane of the ultrafilter (19; 70) has a multi-fiber break if said two stability conditions are not both met.

The further steps described above may be executed after the steps of the preceding aspect.

In a 49th aspect according to the preceding aspect the variation by unit of time (dP/dt) is determined by assigning a respective weight to each received pressure value, with the pressure values received during an initial phase of detection having more weight than pressure values received during an ending phase of detection.

In a 50th aspect according to any one of the preceding five aspects the method comprises the following further steps:
hydraulically isolating the ultrafilter (19; 70);
optionally waiting a given transitory period;
verifying if a variation by unit of time (dP/dt) of values of pressure during a further test interval remains below a further set pressure differential,
determining that the semipermeable membrane of the ultrafilter (19; 70) has a single-fiber break if the above last verifying step is not positively passed.

The further steps described above may be executed after the steps of the preceding aspects 47th or 48th or 49th.

In a 51st aspect according to the preceding aspect verifying if a variation by unit of time (dP/dt) of values of pressure during a further test interval remains below a further set pressure differential comprises verifying if a variation by unit of time (dP/dt) of values of pressure during a further test interval remains below 2 mmHg/s for at least 4 seconds in the first 10 seconds of the further test interval.

In a 52nd aspect according to any one of the preceding five aspects, wherein the method comprises the step of checking a time related parameter, which is one of:
a time necessary to reach a first pressure value (P1'),
a rotation frequency of the waste pump (34, 38),
a pump rotation period of the waste pump (34, 38),
and to compare this detected time related parameter with a corresponding reference threshold, assigning the identification of a multi-fiber break problem in membrane (20) of ultrafilter (19) if the check on the time related parameter is not passed.

A 53rd aspect concerns an extracorporeal blood treatment apparatus (1) comprising:
a supply line (2) having an inlet end connectable to a source of treatment liquid and an outlet end connectable to an inlet port of a blood treatment device (5);
a waste line (13) having an inlet end connectable to an outlet port the blood treatment device (5) and an outlet end connectable to a discharge of used treatment liquid, wherein the supply line (2) and the waste line (13) are part of an hydraulic circuit (100);
an ultrafilter (19) inserted in the supply line (2) and having a semipermeable membrane dividing the ultrafilter (19) into a first chamber (21) and a second chamber (22), the ultrafilter (19) presenting:
a first port connecting a first tract (24) of the supply line (2) to the first chamber (21),
a second port connecting the second chamber (22) to a second tract (26) of the supply line (2);
an air inlet line (30) connected to the first chamber (21) of the ultrafilter (19) or to the first tract (24) of the supply line (2);
at least one waste pump (34, 38) on the waste line (13);
at least one pressure sensor (41) configured for detecting pressure in one of:
the second chamber (22) of the ultrafilter (19),
the second tract (26) of the supply line (2),
the waste line (13);
a controller (50) connected to the waste pump (34, 38) and the at least one pressure sensor (41) and configured to carry out an integrity test procedure comprising the following steps:
filling the first chamber (21) of the ultrafilter (19) with air, optionally by at least commanding opening an air valve or operation an air pump located on the air inlet line (30),
increasing the negative pressure (i.e., rendering the pressure more negative relative to atmospheric pressure present in the environment where the apparatus is installed) or creating a negative pressure (again relative to said atmospheric pressure) in the second chamber (22) of the ultrafilter (19) by operating the waste pump (34, 38),
hydraulically isolating the ultrafilter (19),
receiving pressure values from the at least one pressure sensor (41),
determining a variation by unit of time (dP/dt) of said pressure values detected by the at least one pressure sensor (41) after having hydraulically isolated the ultrafilter (19),
establishing whether the semipermeable membrane of the ultrafilter (19) has either a single fiber break or a multi-fiber break based on said variation by unit of time (dP/dt) of said pressure values detected by the at least one pressure sensor (41).

In a 54th aspect according to the preceding 1st the hydraulic circuit is configurable according to a by-pass configuration, where the supply line (2) is in fluid communication with the waste line (13) via a bypass line bypassing the blood treatment device, and according to a normal configuration, where the outlet end of the supply line (2) communicates with the inlet end of the waste line (13) through the blood treatment device (5).

In a 55th aspect according to the preceding aspect the controller (50) is configured to carry out said integrity test procedure comprising with the hydraulic circuit (100) in by-pass configuration.

In a 56th aspect according to any one of the preceding three aspects said integrity test procedure, which the controller (50) is configured to execute, comprises operating the waste pump (34, 38) in closed-loop as follows:
during said step of filling the first chamber (21) of the ultrafilter (19) with air, achieved by at least opening an air valve or operating an air pump operative on the air inlet line (30), also operating the waste pump (34, 38) based on a first set negative pressure value (P1) which is a desired set value to be reached by pressure sensed by the at least one pressure sensor (41),
after said step of filling the first chamber (21) of the ultrafilter (19) with air, once the first chamber (21) has been emptied from liquid and filled with air, operating the waste pump (34, 38) based on a second set negative pressure value (P2), different from the first set value (P1) and which represents a second desired set value to be reached by pressure sensed by the at least one pressure sensor (41).

In a 57th aspect according to the 56th aspect, the second set negative pressure value (P2) is more negative than the first set pressure value (P1). For example the first set pressure value (P1) is selected in a pressure range between −150 and −450 mm Hg mmHg and the second set pressure value (P2) is selected in a pressure range between −300 and −700 mm Hg mmHg.

In a 58th aspect according to any one of the preceding four aspects the extracorporeal blood treatment apparatus (1) comprises a fresh fluid pump positioned on:
the air inlet line (30), or
the first tract (24) of the supply line (2), between the air injection point and the first port of the ultrafilter (19).

In an 59th aspect according to the preceding aspect the controller (50) is also connected to the fresh fluid pump and configured to operate the fresh fluid pump during said step of filling the first chamber (21) of the ultrafilter (19) with air.

In a 60th aspect according to the preceding aspect wherein the controller is configured to open the air valve (31) with a delay from start of operation of the fresh fluid pump.

In a 61st aspect according to any one of the preceding three aspects, wherein the apparatus (1) comprises a safety pressure sensor (90) located between fresh fluid pump (32) and the first chamber of the ultrafilter (19), wherein the controller (50) is configured to stop operation of fresh fluid pump (32) if a pressure difference or pressure ratio between pressure detected by pressure sensor (41) and pressure detected by safety pressure sensor (90) exceeds an identified safety threshold.

In a 62nd aspect according to any one of the preceding nine aspects the step of establishing whether the membrane of the ultrafilter (19) has either a single fiber break or a multi-fiber break based on said variation by unit of time (dP/dt) of said pressure values detected by the at least one pressure sensor (41) comprises the following first sub-steps:
verifying if two stability conditions are met:
pressure values detected by the at least one pressure sensor (41), optionally at the end of a transitory period subsequent to hydraulic isolation, are below an auxiliary negative pressure threshold (Pt2), and
the variation by unit of time (dP/dt) of said pressure values detected by the at least one pressure sensor (41), optionally at the end of the transitory period is below a set pressure differential (ΔP),
determining that the semipermeable membrane of the ultrafilter (19) has a multi-fiber break if said two stability conditions are not both met.

In a 63rd aspect according to the preceding aspect the auxiliary negative pressure threshold (Pt2) is −350 mmHg.

In a 64th aspect according to any one of the preceding two aspects the set pressure differential (ΔP) is 4 mmHg/s.

In an 65th aspect according to any one of the preceding three aspects the controller (50) is configured to determine said variation by unit of time (dP/dt) assigning a respective weight to each received pressure value, with the pressure values received during an initial phase of detection having more weight than pressure values received during an ending phase of detection.

In a 66th aspect according to any one of the preceding four aspects the step of establishing whether the membrane of the ultrafilter (19) has either a single fiber break or a multi-fiber break based on said variation by unit of time (dP/dt) of said pressure values detected by the at least one pressure sensor (41) comprises the following second sub-steps:
verifying if a variation by unit of time (dP/dt) of said pressure values detected by the at least one pressure sensor (41), during a further test interval, remains below a further set pressure differential (Δp2) for at least a portion of said test interval,
determining that the semipermeable membrane of the ultrafilter (19) has a single-fiber break if the above last verifying step is not positively passed.

In a 67th aspect according to the preceding aspect, the controller is configured to execute the second sub-steps after the first sub-steps.

In a 68th aspect according to any one of the preceding two aspects the step of verifying if a variation by unit of time (dP/dt) of said pressure values detected by the at least one pressure sensor (41) during the further test interval remains below a further set pressure differential (Δp2) for at least a portion of said test interval comprises verifying if the variation by unit of time (dP/dt) of said pressure values detected by the at least one pressure sensor (41) during the further test interval remains below 2 mmHg/s for 4 seconds in the first 10 seconds of the further test interval.

In a 69th aspect according to any one of the preceding three aspects,
said further set pressure differential (Δp2) is a fraction of said set pressure differential (ΔP).

In a 70th aspect according to any one of the preceding four aspects,
said further set pressure differential (Δp2) is less than 70% of said set pressure differential (ΔP).

In a 71st aspect according to any one of the preceding five aspects,
said further set pressure differential (Δp2) is less than or equal to 50% of said set pressure differential (ΔP).

In a 72nd aspect according to any one of the preceding aspects from the 53rd to the 71st, the apparatus (1) further comprises:
at least one inlet valve (39) on the supply line (2) to selectively open and close supply of liquid from the source of treatment liquid;
at least one outlet valve (40) on the waste line (13) to selectively open and close flow of used treatment liquid to the discharge;
a flush line (28) connecting a third port of the first chamber (21) of the ultrafilter (19) to the waste line (13), and
at least one flush valve (29) positioned on the flush line to selectively open and close the first chamber (21) of the ultrafilter (19) to the waste line (13).

In a 73rd aspect according to the preceding aspect the step of hydraulically isolating the ultrafilter (19) comprises the following sub-steps which the controller (50) is configured to execute:
closing at least said inlet valve, outlet valve, flush valve and optionally the air inlet valve,
stopping the waste pump (34, 38).

In a 74th aspect according to the preceding aspect wherein the step of hydraulically isolating the ultrafilter (19) comprises also stopping the fresh fluid pump (32).

A 75th aspect concerns a method of testing the integrity of an ultrafilter membrane of an ultrafilter (19; 70), wherein the ultrafilter membrane separates the ultrafilter (19; 70) into a first and a second chamber (21,22; 72, 73).

A 76th aspect concerns a method of testing the integrity of an ultrafilter membrane of at least one ultrafilter (19; 70) of the extracorporeal blood treatment apparatus (1) according to any one of the preceding aspects from the 1st to the 44th or from the 53rd to the 75th.

In a 77th aspect according to any one of the preceding two aspects, wherein the method comprises executing the following steps:

emptying the first chamber (21; 72) of the ultrafilter (19; 70) from liquid and filling the first chamber (21; 72) with air, after the first chamber (21; 72) has been filled with air, continue extracting liquid from the second chamber (22; 73) of the ultrafilter (19; 70), hydraulically isolating the ultrafilter (19; 70), optionally waiting a given transitory period after hydraulic isolation, receiving pressure values relating to pressure present in the ultrafilter second chamber, determining a variation by unit of time (dP/dt) of said pressure values detected after having hydraulically isolated the ultrafilter (19), establishing whether the semipermeable membrane of the ultrafilter (19) has either a single fiber break or a multi-fiber break based on said variation by unit of time (dP/dt) of said pressure values.

In a 78th aspect according to the preceding aspect, the step of establishing whether the membrane of the ultrafilter (19) has either a single fiber break or a multi-fiber break based on said variation by unit of time (dP/dt) of said pressure values comprises the following first sub-steps:

verifying if two stability conditions are met:
values of pressure in the second chamber (22; 73) of the ultrafilter (19; 70) at the end of the transitory period are below an auxiliary negative pressure threshold, for example below −350 mmHg, and
a variation by unit of time (dP/dt) of said pressure values in the second chamber (22; 73) of the ultrafilter (19; 70) at the end of the transitory period is below a set pressure differential, for example below 4 mmHg/s,
determining that the semipermeable membrane of the ultrafilter (19; 70) has a multi-fiber break if said two stability conditions are not both met.

In a 79th aspect according to the preceding aspect the variation by unit of time (dP/dt) is determined by assigning a respective weight to each received pressure value, with the pressure values received during an initial phase of detection having more weight than pressure values received during an ending phase of detection.

In a 80th aspect according to any one of the preceding three aspects, the step of establishing whether the membrane of the ultrafilter (19) has either a single fiber break or a multi-fiber break based on said variation by unit of time (dP/dt) of said pressure values comprises the following second sub-steps:

verifying if a variation by unit of time (dP/dt) of values of pressure during a further test interval remains below a further set pressure differential,
determining that the semipermeable membrane of the ultrafilter (19; 70) has a single-fiber break if the above last verifying step is not positively passed.

In a 81st aspect according to the preceding aspect verifying if a variation by unit of time (dP/dt) of values of pressure during a further test interval remains below a further set pressure differential comprises verifying if a variation by unit of time (dP/dt) of values of pressure during a further test interval remains below 2 mmHg/s for at least 4 seconds in the first 10 seconds of the further test interval.

In an 82nd aspect according to any one of the preceding aspects each ultrafilter (including if present the auxiliary ultrafilter) is of the type using a semipermeable membrane formed by a bundle of adjacent and substantially coextensive hollow fibers.

In an 83rd aspect according to the preceding aspect the hollow fibers forming the semipermeable membrane are housed in a container and divide the container inner volume into two chambers: one of the two chambers is collectively formed by the volume inside the tubular walls of the plurality of fibers, while the other chamber is collectively formed by the volume outside the tubular walls of the fibers.

DESCRIPTION OF THE DRAWINGS

Aspects of the invention are shown in the attached drawings, which are provided by way of non-limiting example, wherein.

DEFINITIONS

In the present description and claims the following definitions are adopted:

checking integrity of the ultrafilter (or of the auxiliary ultrafilter) semipermeable membrane means checking that the semipermeable membrane does not present one or more breaks in correspondence of any fiber forming the semipermeable membrane structure which could compromise the ability of the semipermeable membrane to properly separate undesired particles such as pollutants, bacteria, endotoxins, from liquid to be filtered; in case of ultrafilter semipermeable membranes formed by a bundle of hollow fibers, checking integrity of the ultrafilter (or of the auxiliary ultrafilter) semipermeable membrane means checking that the tubular wall of all fibers forming the ultrafilter membrane are intact and that therefore the membrane does not present one or more breaks at any fiber tubular wall;

single fiber break means a break compromising the membrane integrity and affecting a single fiber of the ultrafilter membrane;

multi-fiber break or multi-fiber break problem or multi-fiber breaks means a plurality of breaks, i.e.: breaks affecting two or more fibers and compromising the membrane integrity.

CONVENTIONS

In the present description and claims the following conventions are adopted:

the terms downstream and upstream respectively refer to the downstream or upstream position of a component with respect to another component relative to the direction of a fluid flow in a line during normal use of the apparatus;

each pressure value represents the difference between an absolute pressure value and the absolute value of the atmospheric pressure in the ambient where the apparatus is placed; thus, assuming the absolute value of ambient pressure at the apparatus is 760 mmHg, a negative pressure value of for example −300 mmHg represents an absolute pressure value which is =760

−300 mmHg=460 mmHg, i.e., 300 mmHg below the absolute value of the pressure present in the environment surrounding the apparatus.

DETAILED DESCRIPTION

Figure 1:
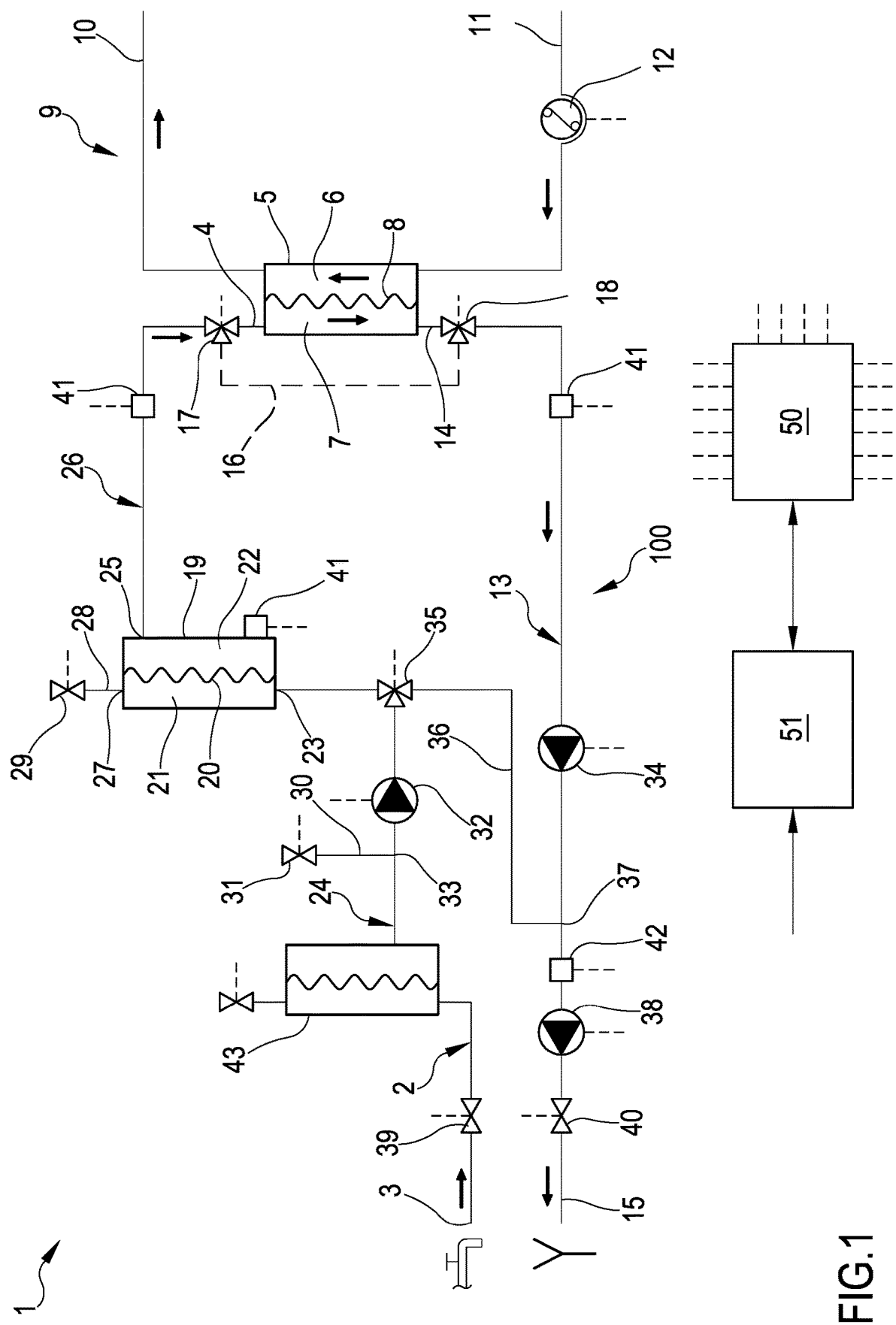
FIG. 1 shows a schematic layout of a dialysis apparatus implementing aspects of the invention.
Figure 2:
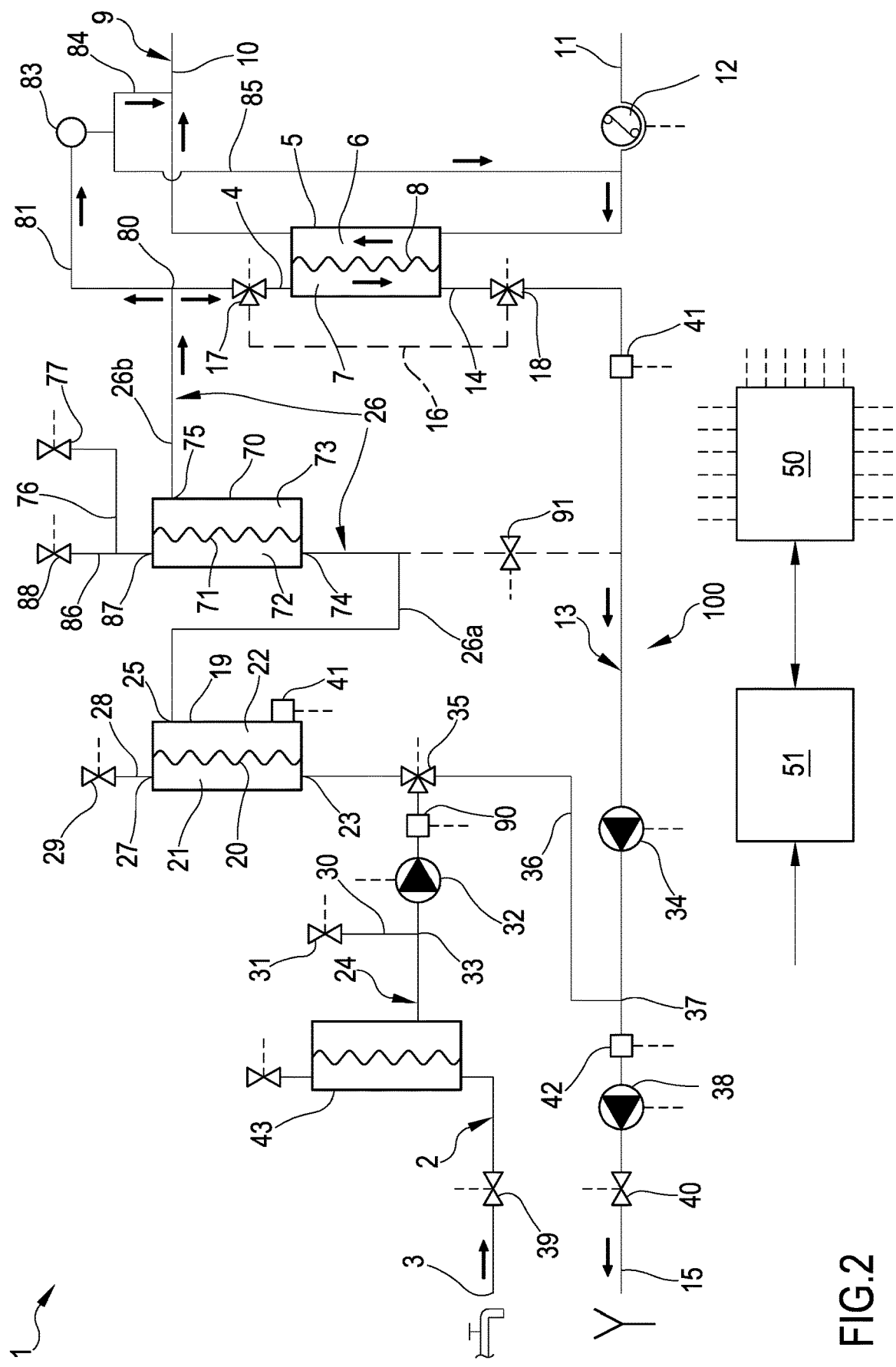
FIG. 2 shows a schematic layout of a hemodiafiltration apparatus implementing aspects of the invention.

An apparatus 1 for extracorporeal treatment of blood—which may implement innovative aspects of the invention—is shown in FIGS. 1 and 2. In particular, the apparatus 1 of FIG. 1 is a dialysis apparatus, while the apparatus 1 of FIG. 2 is a hemodiafiltration apparatus.

The apparatus 1 of FIGS. 1 and 2 includes hydraulic circuit 100 comprising a supply line 2 having an inlet end 3 connectable to a source of treatment liquid. The source of treatment liquid is not shown and may for example be tap water or water coming from a centralized water preparation system. The supply line extends from the inlet end 3 to an outlet end 4 connectable to an inlet port of a blood treatment device 5. For example, in the example of FIG. 1 the blood treatment device 5 comprises a dialyzer, while in the example of FIG. 2 the blood treatment device 5 comprises a hemofilter or a hemodiafilter. Note that the specific nature of the blood treatment device is not relevant to the present invention. The blood treatment device 5 of FIGS. 1 and 2 has a blood chamber 6 and a liquid chamber 7 separated by a semi-permeable membrane 8: the outlet end 4 of the supply line 2 is connected to an inlet of the liquid chamber 7 of the blood treatment device 5. On the other end, the blood chamber 6 is connected to an extracorporeal blood circuit 9 comprising a blood withdrawal line 11 having an end connected with an inlet to the blood chamber 6 and a blood return line 10 having an end connected to an outlet of the blood chamber 6. A blood pump 12 may operate on the extracorporeal blood circuit 9 to pump blood from a patient into the blood withdrawal line, through the blood chamber, into the blood return line and back to the patient. The hydraulic circuit 100 of the apparatus 1 of FIGS. 1 and 2 further comprises a waste line 13 having an inlet end 14 connected to an outlet port the liquid chamber 7 of the blood treatment device 7 and an outlet end 15 connected to a discharge of used treatment liquid. As shown in FIGS. 1 and 2 the supply line 2 and the waste line 13 are configurable according to a normal configuration, where the outlet end 4 of the supply line 2 is connected to the liquid chamber 7 and in fluid communication with the inlet end 14 of the waste line 13. The supply line 2 and the waste line 13 are also configurable according to a by-pass configuration, where the supply line is in fluid communication with the waste line via a bypass line 16 (see dashed line 16 in FIGS. 1 and 2) bypassing the blood treatment device 5 and connecting the outlet end of the supply line with the inlet end of the waste line. The switch from the normal to the bypass configuration may for example be obtained thanks to appropriate valves 17 and 18 or other valves which may be present in the circuit 100. As visible in FIGS. 1 and 2, the apparatus 1 comprises an ultrafilter 19 inserted in the supply line 2 and having a respective semipermeable membrane 20 dividing the ultrafilter into a first chamber 21 and a second chamber 22; the ultrafilter 19 is used for a plurality of treatments and is periodically changed: the ultrafilter 19 may be subject to the integrity test described below to make sure about integrity of the filter membrane before the start of each new treatment; the ultrafilter 19 also presents a first port 23 connecting a first tract 24 of the supply line 2 to the first chamber 21: basically the first tract 24 extends from inlet end 3 to the first port 23 of the ultrafilter 19; the ultrafilter 19 also presents a second port 25 connecting the second chamber 22 to a second tract 26 of the supply line extending from the second port 25 to the outlet end 4 of the supply line. The ultrafilter 19 may also present a third port 27 connecting the first chamber 21 to a flushing line 28 connectable to the waste line 13: in the examples of FIGS. 1 and 2, the flushing line 28 has at least a valve 29 for selectively opening and closing the flushing line and thus selectively forming or stopping a fluid communication between the first chamber 21 and the waste line 13.

The apparatus 1 also includes an air inlet line 30: the air inlet line of the example of FIGS. 1 and 2 is connected to the first tract 24 of the supply line 2 at air injection point 33 and presents an air inlet valve 31, which may be selectively opened or closed to respectively allow or prevent admission of air into the supply line 2 and towards the ultrafilter 19; note that instead or in addition to the air valve 31 an occlusive air pump may be used in order to selectively control admission of air into the air inlet line 30. Alternatively, the air inlet line 30 may be directly connected to the first chamber 21 of the ultrafilter 19. As shown in FIGS. 1 and 2, the apparatus 1 further comprises a fresh fluid pump 32 on the supply line 2 and a waste pump 34 on the waste line 13. In the examples shown, the fresh fluid pump 32 is positioned on the first tract 24 of the supply line 2, downstream to air injection point 33 and upstream the ultrafilter 19. Note that in the examples shown a three-way valve 35 may be positioned at the end of a further by-pass line 36 connecting the waste line 13 and the supply line 2: specifically, the three way valve 35 is positioned between the fresh fluid pump 32 and the ultrafilter 19, while the further by-pass line 36 extends between the three-way valve 35 and a junction point 37 in the-waste line 13, positioned between the waste pump 34 and the outlet end 15 of the waste line.

Also note that the apparatus 1 may comprise an auxiliary waste pump 38 operative on the waste line 13 and positioned between the waste pump 34 and the outlet end 15 of the waste line. Additionally, a general water inlet valve 39, operable to selectively open and close admission of fresh liquid (fresh water) into the supply line 2, may be present at the inlet end 3 of the supply line 2, and a general waste outlet valve 40, operable to selectively open and close discharge of waste liquid out of the waste line 13 may be present at the outlet end of waste line 13.

The apparatus 1 of FIGS. 1 and 2 furthermore comprises one or more pressure sensors as described below. In greater detail, at least one pressure sensor 41 is configured for directly or indirectly detecting pressure in the second chamber of the ultrafilter. At this purpose, the pressure sensor 41 may be directly connected to the second chamber 22 of the ultrafilter 19 or it may be positioned on the second tract 26 of the supply line or on the waste line in correspondence of the tract of waste line extending between the inlet end 14 and the waste pump 34. As shown in FIGS. 1 and 2, the apparatus may include an auxiliary waste pump 38 and, in this case, an auxiliary pressure sensor 42 is positioned on the waste line between the waste pump 34 and the auxiliary waste pump 38.

Again with reference to FIGS. 1 and 2 the apparatus may include an optional water inlet ultrafilter 43, which is operative on the supply line immediately downstream the water inlet valve 39: also the water inlet ultrafilter 43 may be periodically changed and, in the example herein described, is not subject to any integrity test procedure.

Finally, the apparatus of FIGS. 1 and 2 includes a controller 50. The controller 50 is connected to the valves, pumps and pressure sensors described above and configured to control operation of the apparatus 1. In detail, the controller 50 is connected to the air valve 31, the waste pump 34, (if present) the waste pump 38, the pressure sensor 41 and (if present) the auxiliary pressure sensor 42. The controller 50 may be connected to a user interface 51 and be configured to receive inputs from an operator and then perform execution of an extracorporeal blood treatment based on the operator's input: the present disclosure does not provide further details on the controller role in the handling of the blood treatment as this is not relevant to the present invention.

A safety pressure sensor 90 is located between fresh fluid pump 32 and three-way valve 35. The controller may be configured to stop operation of fresh fluid pump 32 once the pressure difference between pressure detected by sensor 41 and pressure detected by safety pressure sensor 90 exceeds an identified safety threshold to prevent from pressurize air in chamber 21. Of course pressure ratio between pressure detected by sensor 41 and pressure detected by safety pressure sensor 90 may be used in place of pressure difference.

At the beginning of each new treatment, or periodically every given number of treatments, the controller 50 is configured to automatically (or upon operator's request) execute an ultrafilter integrity test procedure as herein described in further detail. Note that before initiating the ultrafilter integrity test procedure, the controller 50 may also be configured or programmed to execute a number of per se known phases such as coordinating the filling and flushing of the hydraulic circuit and operate valves 17 and 18 to put the hydraulic circuit and in particular the supply line and the waste line in a by-pass configuration (see dash lines in FIGS. 1 and 2 by-passing the blood treatment device 5).

With the supply line and waste line in the by-pass configuration, the controller 50 is configured or programmed to execute an integrity test procedure for checking whether the membrane 20 of the ultrafilter 19 is intact or not.

Figure 3:
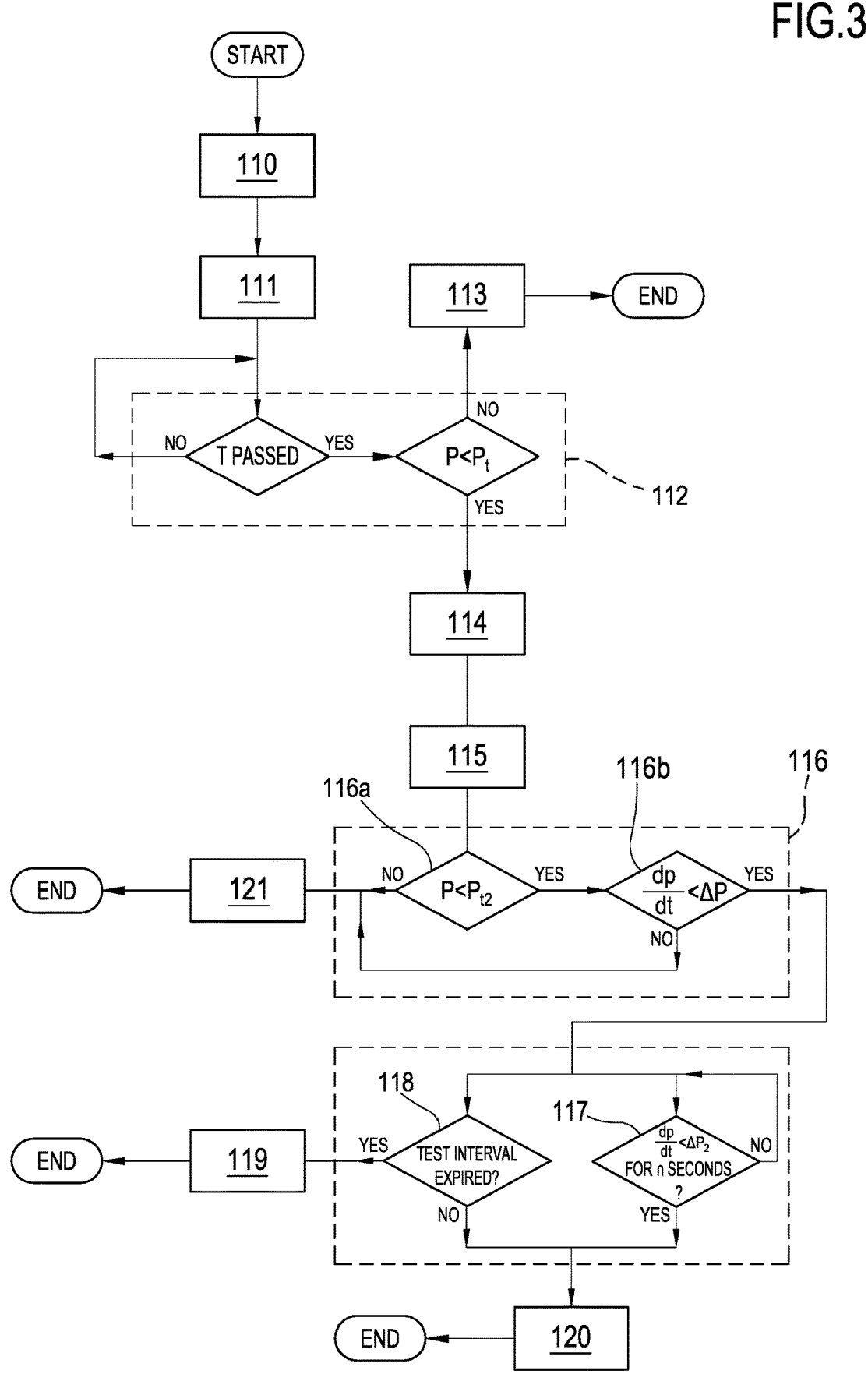
FIG. 3 shows a block diagram of a method of testing the integrity of an ultrafilter membrane of an ultrafilter, according to aspects of the invention.

With reference now to the flowchart of FIG. 3, the integrity test procedure comprises the following steps.

Initially, the controller 50 causes filling with air of the first chamber 21 of the ultrafilter 19 (step 110 in FIG. 3): this is achieved by opening the air valve 31 (or possibly operating the air pump 31) and creating a suction of air towards said first chamber of the ultrafilter. In order to create an air flow through the air inlet line 30 and towards the ultrafilter first chamber 21, the fresh fluid pump 32 and the waste pump 34 are is also operated, for example when opening the air valve or even before opening the air valve 31 (or in case an air pump 31 is used when operating or before operating the air pump 31). For example, the fresh fluid pump 32 may be operated at a given angular speed while the waste pump 34 may be operated in closed loop based on a first set pressure P1 which is a desired value to be sensed at the pressure sensor 41. In an example, the waste pump 34 may be operated in closed loop with the first set pressure P1 at pressure sensor 41 set equal to −350 mmHg as control loop parameter (i.e. 350 mmHg below the atmospheric pressure present in the ambient where the apparatus is installed). In a case like in FIGS. 1 and 2 where two pumps are present in the waste line 13, then both waste pump 34 and auxiliary waste pump 38 may (during this phase) be operated in closed loop based on the first set desired pressure P1 to be sensed at the pressure sensor 41 for pump 34 and to be sensed at auxiliary pressure sensor 42 for pump 38. The first set pressure value P1 (e.g., −350 mmHg) is in this case the same for both pumps.

After filling the first chamber with air, the controller 50 is configured to form a negative pressure or further increase the value of negative pressure in the second chamber of the ultrafilter (step 111 in FIG. 3—as always negative pressure is intended relative to the atmospheric pressure present in the ambient where the machine operates; therefore increasing the value of the negative pressure means making the pressure further below the atmospheric pressure present in the environment where the apparatus is installed) by continuing to operate the waste pump, or the waste pumps if two waste pumps are present. In greater detail, after said step of filling the first chamber of the ultrafilter, i.e., once the first chamber has been completely emptied from liquid and filled with air, the controller 50 controls operation of the waste pump 34 in closed loop based on a second set negative pressure value P2 (e.g., −600 mmHg), which shall be reached by pressure sensed by the pressure sensor 41 and which is more negative than the first pressure value P1 (again relative to ambient pressure present where the apparatus is installed). In a case like in FIGS. 1 and 2 where two pumps are present in the waste line 13, then both waste pump 34 and auxiliary waste pump 38 may (during this phase) be operated in closed loop based on second set negative pressure value P2 to be sensed at the pressure sensor 41 for pump 34 and to be sensed at auxiliary pressure sensor 42 for pump 38.

For example, the first set pressure value P1 may be selected in a pressure range between −150 and −450 mm Hg, while the second set pressure value P2 may be selected in the range between −300 and −700 mm Hg (with the condition that the second pressure value be at least 100 mm Hg more negative than the first set pressure value).

More in general, the first set pressure value P1 may be selected in a pressure range allowing to drain the ultrafilter at moderate flow rates in order to avoid excessive stress on the membrane; the second set pressure value P2 may be selected such as to have an appreciable delta pressure with no residual flow, thus avoiding excessive stresses on the membrane and degasification that could cause exceeding the membrane bubble point (thus resulting into possible false alarms).

After the above described two steps, the controller provides for verifying (step 112 in FIG. 3), while the waste pump 34 is running (or both the waste pump 34 and the waste pump 38 are still running), if the pressure sensed by the pressure sensor 41 reaches a set negative pressure threshold Pt, for then determining (step 113) that the ultrafilter semipermeable membrane has a multi-fiber break if the pressure sensed by the pressure sensor 41 during the verification step does not reach the set negative pressure threshold Pt within a set time interval T. This verification step may include checking pressure at the pressure sensor 41 after expiration of time interval T; alternatively one may envisage to measure the time interval at which the negative pressure threshold Pt is reached. In any case, if in this step the threshold pressure Pt is not reached or reached too late, the controller 50 concludes that there is a multi-fiber break problem for the membrane of the ultrafilter 19. The set negative pressure threshold has a negative value intermediate between said first set pressure value and said second set pressure value. For example if the first pressure value is set at −350 mm Hg and the second pressure value is set at −600 mm Hg, the pressure threshold may be equal to −500 mm Hg. The set pressure threshold has a negative value aimed at identifying multi-fiber breaks, thus providing an early detection.

The time interval (i.e., the interval by which the pressure sensed by the pressure sensor 41 should reach the set negative pressure threshold to exclude a multi-fiber break of the ultrafilter membrane) is counted by the controller starting from the moment at which the controller imposes the second negative pressure as setting to control the waste pump 34 (or to both waste pumps 34 and 38). This time interval lasts 10 to 60 seconds, for example 30 seconds.

According to aspects of the invention, the integrity test procedure may further comprise the following additional steps which the controller is configured to execute after steps 110 to 113 described above.

In detail, at step 114 the controller is configured to command the appropriate components for hydraulically isolating the ultrafilter: as it is known to the skilled person hydraulic isolation of the ultrafilter may take place in different ways depending upon the specific design of the hydraulic circuit 100. For example, with reference to FIG. 1, the controller may command closure of at least valves 29, 40 and 35 (or other equivalent valves blocking flow to the first chamber 21) and stop of the pumps 32, 34 and 38. Then, the controller (step 115 in FIG. 3) is configured for receiving pressure values detected by the pressure sensor 41 at the end of a given transitory period after having hydraulically isolated the ultrafilter; subsequently, the controller is configured for verifying (step 116) if two stability conditions (116a, 116b) are met, namely that the pressure values detected by pressure sensor 41 at the end of the transitory period be below an auxiliary negative pressure threshold Pt2 (for example below −350 mmHg, again relative to atmospheric pressure present in the ambient where the machine is installed), and that the variation by unit of time (dP/dt) of the pressure values detected by the at least one pressure sensor 41 at the end of the transitory period be sufficiently small and specifically be below a set pressure differential $\Delta P$, for example below a value comprised between 3 to 6 mmHg, and in a presently preferred variant below 4 mmHg/s. Note that in a preferred embodiment the auxiliary negative pressure threshold Pt2 is less negative than the pressure threshold Pt (relative to atmospheric pressure present in the ambient where the machine is installed, thus Pt2 is closer than Pt to atmospheric pressure). Furthermore, the set pressure differential $\Delta P$ is chosen at a value suitable to detect multi-fiber breaks; in addition and in accordance with a further aspect, the controller 50 may be configured to sample the dP/dt values giving more weight to pressure values at the beginning of the detection phase when delta pressure is at its highest values (for example using a low-pass filter). The controller 50 (step 121) is configured for then determining that the semipermeable membrane of the ultrafilter 19 has a multi-fiber break if the two conditions (steps 116a, 116b) are not both met.

The integrity test procedure may also comprise the following further steps (steps 117-120 in FIG. 3) which the controller is configured to execute in order to determine if the membrane 20 of the ultrafilter 21 has a single fiber break. The further steps 117-120 described below are, in one aspect of the invention, executed after having verified that membrane 20 of the same ultrafilter 21 has no multi-fiber breaks (steps 110-113 and steps 114-116). In other words, the check for a possible single fiber break may be made as last check, thereby avoiding to carry out unnecessary steps if it is concluded that there is a higher ranking problem, namely a multi-fiber break. According to this aspect, the integrity test procedure, may therefore be configured to hydraulically isolate the (or maintain hydraulic isolation of) ultrafilter 19 and then receiving pressure values detected by the pressure sensor 41 during a further test interval after said transitory period following hydraulic isolation of the ultrafilter. In other words, while steps 114-115 are executed after hydraulic isolation of the ultrafilter but during pressure stabilization, the following steps are executed after having waited a relatively long time interval (longer than said transitory period) after which it is expected that, absent fiber integrity problems, pressure should be highly stable. Thus, the controller 50 is configured, after waiting for expiration of the transitory period and during the further test interval, for verifying if a variation by unit of time (dP/dt) of said pressure values detected by the pressure sensor 41 during the further test interval remains below a further set pressure differential $\Delta p2$ during at least a portion lasting n seconds of the further test interval (step 117). The further set pressure differential $\Delta p2$ may be in the range between 1 and 3 mmHg and in a specific example it may be equal to 2 mmHg. More in general, the further set pressure differential $\Delta p2$ is set in order to detect a single broken fiber ($\Delta p2$ may in practice be a fraction, e.g., 50% compared to said set pressure differential $\Delta P$). The test interval is relatively short and may last 5 to 30 seconds, for instance 10 seconds; therefore, the controller checks if dp/dt stays below for example 2 mmHg during a portion of e.g., 4 seconds of the test interval (step 117) and also checks expiration of the test interval (118); the controller is configured to then establish that the membrane of the ultrafilter has a single-fiber break (step 119) if the check of step 117 is not positively passed before expiration of the test interval (step 118), i.e., before expiration of the 10 seconds in this example. Otherwise, if before expiration of the test interval, dp/dt stays below $\Delta p2$ (in this example below 2 mmHg) for n seconds (in this example for consecutive 4 seconds), then it is determined that the ultrafilter membrane is intact (step 120).

The apparatus of FIG. 2 has, in addition to the ultrafilter 20, an auxiliary ultrafilter 70 inserted in the second tract 26 of the supply line 2. The auxiliary ultrafilter 70 is used for a plurality of treatments and is periodically changed: for this reason also ultrafilter 70 may be subject to the integrity test described below to make sure about integrity of the filter membrane before the start of each new treatment. The auxiliary ultrafilter 70 has a semipermeable membrane 71 dividing the auxiliary ultrafilter into a respective first chamber 72 and a respective second chamber 73: the auxiliary ultrafilter may be structurally identical to the ultrafilter 20. The auxiliary ultrafilter 70 presents a first port 74 connecting, via first portion 26a of second tract 26, the first chamber 72 to second port 25 of the ultrafilter 19 second chamber 22. The auxiliary ultrafilter 70 also includes a respective second port 75 connecting the second chamber 73 of the auxiliary ultrafilter 70 to a second portion 26b of the second tract 26 of the supply line 2. It should be noted that in the non-limiting example of FIG. 2, an infusion line 81 may depart from the second portion 26b of the second tract 26 of line 2: in particular in the example of FIG. 2, infusion line 81 departs from bifurcation point 80 and may lead to an infusion port 83, which may be present on an accessible portion of the apparatus 1 (for example on the apparatus front panel), to which one or more replacement fluid lines 84 and 85 may be connected. Replacement fluid lines 84 and 85 shown in FIG. 2 thereby bring to the extracorporeal blood circuit fresh fluid filtered through the ultrafilters 21 and 70. An auxiliary air inlet line 76 is connected to the first chamber 72 of the auxiliary ultrafilter 70 or to the first portion 26a of the second tract of the supply line: the air inlet line 76 is provided with a respective auxiliary air valve 77 (or with an auxiliary occlusive air pump) in order to selectively open and close admission of air via the air inlet line 76 under the control of controller 50 and allow air filling of the first chamber of the auxiliary ultrafilter during execution of the integrity test procedure of the semipermeable membrane 71. In the alternative embodiment of FIG. 2, pressure sensor 41 may be configured for detecting pressure in one of the second chamber of the ultrafilter, the second portion of the second tract of the supply line, or the waste line (this last alternative is shown in FIG. 2). An auxiliary flush line 86 connects a third port 87 of the first chamber of the auxiliary ultrafilter 70 to the waste line, and an auxiliary flush valve 88 is positioned on the flush line 86 to selectively open and close the first chamber of the auxiliary ultrafilter 70 to the waste line.

Figure 4:
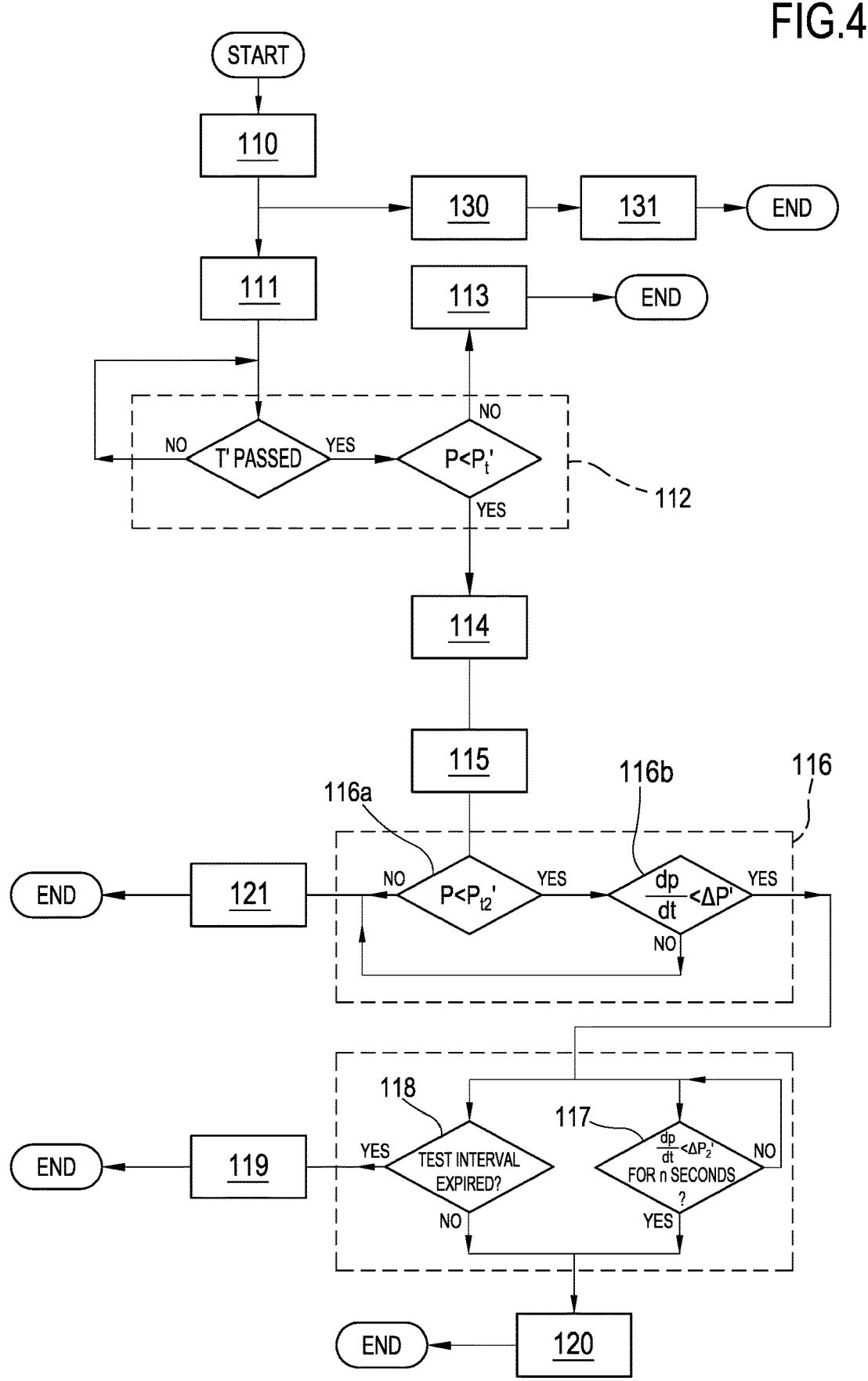
FIG. 4 shows a block diagram of a method of testing the integrity of an ultrafilter membrane of an auxiliary ultrafilter, according to other aspects of the invention.

The controller 50 is configured to carry out, with the supply line and the waste line in by-pass configuration, an auxiliary integrity test procedure on the auxiliary ultrafilter 70. The auxiliary test procedure on the ultrafilter is also represented in FIG. 4: in any case most steps of the auxiliary test procedure are similar to those of the test procedure conducted on the ultrafilter 20.

In particular, according to the auxiliary integrity test procedure, the controller 50 initially causes filling with air of the first chamber 72 of the ultrafilter 70 (step 110 in FIG. 4): this is achieved by opening the air valve 77 (or activating an air pump on the auxiliary air inlet line) and creating a suction of air towards said first chamber of the ultrafilter. In order to create an air flow through the air inlet line 76 and towards the ultrafilter first chamber 72, the waste pump 34 or the waste pumps 34 and 38 is/are operated, for example when opening the air valve or even before opening the air valve 77 (in case an occlusive air pump is used in place of the air valve the pump 34 or the pumps 34 and 38 may be operated in synchronism with the occlusive air pump or even before starting operation of the occlusive air pump). The waste pump 34 may be operated in closed loop based on a first set pressure $P1'$ which is a desired value to be sensed at the pressure sensor 41. In an example, the waste pump 34 may be operated in closed loop with the first set pressure $P1'$ at pressure sensor 41 set equal to −300 mmHg as control loop parameter. In a case like in FIG. 2, where two pumps are present in the waste line 13, then both waste pump 34 and auxiliary waste pump 38 may (during this phase) be operated in closed loop based on the first set desired pressure $P1'$ to be sensed at the pressure sensor 41 for pump 34 and to be sensed at auxiliary pressure sensor 42 for pump 38. The first set pressure value $P1'$ (e.g., −300 mmHg) may be the same for both pumps.

In case pressure sensor 41 immediately reaches the $P1'$ first set pressure value, thus causing the waste pump 34 (and if present also pump 38) to decelerate or stop without removing the water supposed to be still present in chamber 72, this identifies that the chamber 72 is in reality already empty. Thus, the controller 50 may also be configured, in accordance with an ancillary aspect, to check a time related parameter (step 130) such as the time necessary to reach the first pressure value $P1'$ or the pump rotation frequency of waste pump 34 (and/or 38), or the pump rotation period of pump 34 (and/or 38), and compare this detected time related parameter with a corresponding reference threshold, assigning the identification of a multi-fiber break problem in membrane 20 of ultrafilter 19 if the check on the time related parameter is not passed (step 131). In practice, if the time necessary to reach the first pressure value $P1'$ is too short, or if the frequency of one or both the waste pumps is too high, or if the pump rotation period of one or both the waste pumps is too small, then it is concluded that there is a multi-fiber break of the membrane 19 of ultrafilter 20, which for some reason was not detected before. Then, after filling the first chamber 72 with air, the controller 50 is configured to form a negative pressure or increase the negative pressure in the second chamber 73 of the ultrafilter (step 111 in FIG. 4—negative pressure is intended relative to the atmospheric pressure present in the ambient where the machine operates; therefore increasing the value of the negative pressure means making the pressure further below the atmospheric pressure present in the environment where the apparatus is installed) by continuing to operate the waste pump or the waste pumps if two waste pumps are present. In greater detail, after said step of filling the first chamber of the ultrafilter with air, i.e., once the first chamber has been completely emptied from liquid and filled with air, the controller 50 controls operation of the waste pump 34 in closed loop based on a second set negative pressure value $P2'$ (e.g., −600 mmHg), which shall be reached by pressure sensed by the pressure sensor 41 and which is more negative than the first pressure value $P1'$. In a case like in FIG. 2 where two pumps are present in the waste line 13, then both waste pump 34 and auxiliary waste pump 38 may (during this phase) be operated in closed loop based on second set negative pressure value $P2'$ to be sensed at the pressure sensor 41 for pump 34 and to be sensed at auxiliary pressure sensor 42 for pump 38.

The first set pressure value $P1'$ may be selected in a pressure range between −150 and −450 mm Hg, while the second set pressure value $P2'$ may be selected in the range between −300 and −700 mm Hg (with the condition that the second pressure value be at least 100 mm Hg more negative than the first set pressure value).

More in general, the first set pressure value $P1'$ may be selected in a pressure range allowing to drain the ultrafilter at moderate flow rate in order to avoid excessive stress on the membrane; the second set pressure value $P2'$ may be selected to form a sufficient delta pressure with no residual flow, also avoiding excessive stress on the membrane and degasification that could cause exceeding the membrane bubble point exceeding. At the end of the draining phase of ultrafilter 70, the controller may be configured to put first port 74 in communication with line 15, for example by opening an ancillary by-pass valve 91 placed on a line connecting the first tract 26a with the waste line 15. The controller opens the ancillary by-pass valve 91 for a short time frame (e.g., 1 to 5 seconds) to ensure the complete draining of the ultrafilter 70 from top to bottom.

After the above described two steps, the controller provides for verifying (step 112 in FIG. 3), while the waste pump 34 is running (or both the waste pump 34 and the waste pump 38 are still running), if the pressure sensed by the pressure sensor 41 reaches a set negative pressure threshold $Pt'$, for then determining (step 113) that the ultrafilter membrane 71 has a multi-fiber break if the pressure sensed by the pressure sensor 41 during the verification step does not reach the set negative pressure threshold $Pt'$ within a set time interval $T'$. This verification step may include checking pressure at the pressure sensor 41 after expiration of time interval $T'$; alternatively, one may envisage to measure the time interval at which the negative pressure threshold $Pt'$ is reached. In any case, if in this step the threshold pressure $Pt'$ is not reached or reached too late, the controller 50 concludes that there is a multi-fiber break problem for the semipermeable membrane 71 of the ultrafilter 70. The set negative pressure threshold $Pt'$ has a negative value intermediate between said first set pressure value $P1'$ and said second set pressure value $P2'$. For example if the first pressure value $P1'$ is set at −300 mm Hg and the second pressure $P2'$ at −600 mm Hg, the pressure threshold $Pt'$ may be equal to −450 mm Hg. In more general terms, the pressure threshold Pt' may be selected to have a value which is a negative value intermediate between said first set pressure value P1' and said second set pressure value P2' and which aims at early identification of multi-fiber breaks.

The set time interval T' (i.e., the interval by which the pressure sensed by the pressure sensor 41 should reach the set negative pressure threshold Pt' to exclude a multi-fiber break of the ultrafilter membrane) is counted by the controller starting from the moment at which the controller imposes the second negative pressure P2' as setting to control the waste pump 34 (or to both waste pumps 34 and 38). This time interval T' may last 10 to 60 seconds, for example of 30 seconds.

According to aspects of the invention, the auxiliary integrity test procedure may further comprise the following additional steps which the controller 50 is configured to execute after steps 110 to 113 described above.

In detail, at step 114 the controller 50 is configured to command the appropriate components to hydraulically isolating the ultrafilter 70: for example, with reference to FIG. 2, the controller may command closure of valves 35, 40 and 88 (and possibly also valve 77) and stop of the pumps 32, 34 and 38. Then, the controller (step 115 in FIG. 4) is configured for receiving pressure values detected by the pressure sensor 41 at the end of a given transitory period after having hydraulically isolated the auxiliary ultrafilter 70; subsequently, the controller 50 is configured for verifying (step 116) if two stability conditions (116a, 116b) are met, namely that the pressure values detected by pressure sensor 41 at the end of the transitory period be below an auxiliary negative pressure threshold Pt2' (for example below −350 mmHg), and that the variation by unit of time (dP/dt) of the pressure values detected by pressure sensor 41 at the end of the transitory period be sufficiently small and specifically be below a set pressure differential ΔP', for example below 4 mmHg/s. Note that in a preferred embodiment the auxiliary negative pressure threshold Pt2' is less negative than the pressure threshold Pt' and the set pressure differential ΔP' is set in order to detect multi-fiber breaks (example 4 mmHg); in addition and in accordance with a further aspect, the controller 50 may be configured to sample the dP/dt values giving more weight to pressure values at the beginning of the detection phase when delta pressure is at its highest values (for example using a low-pass filter). The controller 50 (step 121) is configured for then determining that the membrane of the ultrafilter 19 has a multi-fiber break if the two conditions (steps 116a, 116b) are not both met.

The auxiliary integrity test procedure on ultrafilter 70 may also comprise the following further steps which the controller is configured to execute in order to determine if the membrane 71 has a single fiber break. The further steps described below are, in one aspect of the invention, executed after having verified that membrane 70 of the same ultrafilter 71 has no multi-fiber breaks (steps 110-113 and steps 114-116). In other words, the check for a possible single fiber break may be made as last check on the ultrafilter 70, thereby avoiding to carry out unnecessary steps if it is concluded that there is a higher ranking problem, namely a multi-fiber break. According to this aspect, the integrity test procedure, may therefore be configured to hydraulically isolate (or maintain hydraulic isolation of) the auxiliary ultrafilter 70 and then receiving pressure values detected by the pressure sensor 41 during a further test interval after the transitory period following hydraulic isolation of the ultrafilter 70. In other words, while steps 114-115 are executed after hydraulic isolation of the ultrafilter 70 but during pressure stabilization, the following steps are executed after having waited a relatively long transitory period after which it is expected that—absent fiber integrity problems—pressure should be highly stable. Thus, the controller 50 is configured, after waiting for expiration of the transitory period, for verifying if a variation by unit of time (dP/dt) of said pressure values detected by the pressure sensor 41 during the further test interval remains below a further set pressure differential Δp2' during at least a portion lasting n seconds of the further test interval (step 117). The further set pressure differential Δp2' may be in the range between 1 and 3 mmHg and in a specific example it may be equal to 2 mmHg. More in general, the further set pressure differential Δp2' is set in order to detect a single broken fiber (Δp2' may in practice be a fraction, e.g., 50% compared to said set pressure differential ΔP'). The test interval is relatively short and may last 5 to 30 seconds, for instance 10 seconds; therefore, the controller checks if dp/dt stays below for example 2 mmHg during a portion of e.g., 4 seconds of the test interval (step 117) and also checks expiration of the test interval (118); the controller is configured to then establish that the membrane of the auxiliary ultrafilter 70 has a single-fiber break (step 119) if the check of step 117 is not positively passed before expiration of the test interval (step 118), i.e., before expiration of the 10 seconds in this example. Otherwise, if before expiration of the test interval, dp/dt stays below Δp2' (in this example below 2 mmHg) for n seconds (in this example for consecutive 4 seconds), then it is determined that the auxiliary ultrafilter membrane is intact (step 120).

Controller 50

As already indicated the apparatus according to the invention makes use of at least one controller 50. This controller may comprise a digital processor (CPU) with memory (or memories), an analogical type circuit, or a combination of one or more digital processing units with one or more analogical processing circuits. In the present description and in the claims it is indicated that the controller is "configured" or "programmed" to execute certain steps: this may be achieved in practice by any means which allow configuring or programming the controller. For instance, in case of a controller comprising one or more CPUs, one or more programs are stored in an appropriate memory: the program or programs containing instructions which, when executed by the controller, cause the controller to execute the steps described and/or claimed in connection with the controller. Alternatively, if the controller is of an analogical type, then the circuitry of the controller is designed to include circuitry configured, in use, to process electric signals such as to execute the controller steps herein disclosed.

Method of Testing the Integrity of an Ultrafilter Semipermeable Membrane

The invention also concerns a method of testing the integrity of an ultrafilter membrane of an ultrafilter. The ultrafilter may be part of an extracorporeal blood treatment apparatus. For instance, the method may be used for testing the integrity of the membrane of one or all the ultrafilters described above in connection with the apparatus of FIG. 1 or the apparatus of FIG. 2. In accordance with one aspect, the method described below may be implemented by any apparatus 1 described above or claimed in any one of the appended claims.

The method of the invention detects if the ultrafilter membrane is subject to multi-fiber breaks or to a single fiber break.

The method comprises executing the following steps (please refer again to FIG. 3 and to FIG. 4):

step 110: emptying the first chamber of the ultrafilter from liquid and filling the first chamber with air, step 111: after the first chamber has been filled with air, continue extracting liquid from the second chamber of the ultrafilter, step 112: verifying, while extracting liquid from the second chamber of the ultrafilter, if the pressure in the ultrafilter second chamber reaches a set negative pressure threshold, step 113: determining that the ultrafilter semipermeable membrane has a multi-fiber break if the pressure in the second chamber during the step of extracting liquid does not reach said set negative pressure threshold within a set time interval. The set time interval of said verifying step is a set time interval calculated from start of the step of extraction of liquid from the second chamber, or calculated from end of filling with air the first chamber of the ultrafilter under test.

After conclusion of steps 110-113, if no multi-fiber break has been detected the method continues with the following further steps:

step 114: hydraulically isolating the ultrafilter;

step 115: waiting a given transitory period;

step 116: verifying if two stability conditions are met, one stability condition checking the ability to reach a certain negative pressure, while the other condition checking the stability of pressure.

In greater detail step 116 comprises the following sub-steps:

sub-step 116a: verifying if the values of pressure in the second chamber of the ultrafilter at the end of the transitory period are below an auxiliary negative pressure threshold, for example below −300 or below −350 mmHg, and sub-step 116b: verifying if the variation by unit of time (dP/dt) of the pressure values in the second chamber of the ultrafilter at the end of the transitory period is below a set pressure differential, for example below 4 mmHg/s.

If the verifications of sub-steps 116a and 116b are not both positively passed, the method determines that the membrane of the ultrafilter has a multi-fiber break. In other words, it is sufficient that one of the two conditions of sub-steps 116a, 116b not be met to conclude for the presence of a multi-fiber break.

Finally, after conclusion of steps 110-113, and in one aspect, after conclusion also of steps 114-116, the method provides for a sequence of steps, namely steps 117-120) aimed at determining the possible presence in the membrane of a single fiber break. In particular, the method may comprise the following additional steps:

step 118: monitoring expiration of a further test time interval after said given transitory period;

step 117: verifying if a variation by unit of time dP/dt of values of pressure during the further test interval after said given transitory period remains below a further set pressure differential; for example it may be checked if dP/dt during the further test interval remains below 2 mmHg/s, for at least a portion of said further test interval, for example for 4 s in the first 10 s of the further test interval.

Then, at step 119, it is determined that the membrane of the ultrafilter has a single-fiber break if the above last condition is not met. If, instead, the above last condition is met, the method provides for informing an operator or for issuing a corresponding signal to the controller of the apparatus 1 (step 120).

If the above test method is applied to an ultrafilter (for example the auxiliary ultrafilter 70 of FIG. 2) having the first chamber connected with the second chamber of another already tested ultrafilter (for example ultrafilter 19 in FIG. 2), the behavior of the draining pump 34 (and 38) may be monitored and used to identify a multi-broken fiber in the membrane of the first ultrafilter, causing the first chamber of the ultrafilter under testing to be empty when expected to be still full of liquid (steps 130, 131). For example, the method may include to check a time related parameter (step 130) such as the time necessary to reach P1' or the pump rotation frequency, or the pump rotation period, and compare this detected time related parameter with a corresponding reference threshold, assigning the identification of a multi-fiber break problem in the membrane of ultrafilter 19 if the check on the time related parameter is not passed (step 131).

Finally, according to aspects of the invention, a method of testing ultrafilters may use only steps 110, 111 and 114 to 120 (without steps 112-113) to identify whether an hydraulically isolated ultrafilter has a single fiber break or a multiple fiber break, in particular by first creating a negative pressure in the second chamber of the ultrafilter (e.g., executing steps 110 and 111 described above) and then detecting the behavior of derivative dp/dt to decide whether the ultrafilter membrane is intact or has a single fiber break or multiple fiber breaks, as described above in connection with steps 116a and 116b and with steps 117 and 118, and as indicated in aspects from 53rd to 81st of the summary section.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. An extracorporeal blood treatment apparatus comprising:

a supply line including an inlet end connectable to a source of treatment liquid and an outlet end connectable to an inlet port of a blood treatment device;

a waste line including an inlet end connectable to an outlet port of the blood treatment device and an outlet end connectable to a discharge of used treatment liquid;

an ultrafilter inserted in the supply line and including a semipermeable membrane dividing the ultrafilter into a first chamber and a second chamber, the ultrafilter including:

a first port connecting a first tract of the supply line to the first chamber, and a second port connecting the second chamber to a second tract of the supply line;

an air inlet line connected to the first chamber of the ultrafilter or to the first tract of the supply line;

at least one waste pump on the waste line;

at least one pressure sensor configured to detect a pressure in one of:

the second chamber of the ultrafilter, the second tract of the supply line, or the waste line; and a controller in communication with the at least one waste pump and with the at least one pressure sensor and, as part of an integrity test procedure, wherein the controller is configured to:
cause filling of the first chamber of the ultrafilter with air, by at least commanding an opening of an air valve or an operation of an air pump located on the air inlet line, after causing the first chamber to fill with air, increasing an existing negative pressure in the second chamber or creating a negative pressure in the second chamber of the ultrafilter by operating the waste pump,
verify if, while the waste pump is running, the pressure sensed by the at least one pressure sensor reaches a set negative pressure threshold (Pt), and
determine that the ultrafilter semipermeable membrane has a multi-fiber break if pressure sensed by the at least one pressure sensor during said verification does not reach said set negative pressure threshold (Pt) within a set time interval (T), wherein the pressure is considered relative to the atmospheric pressure present in a location where the apparatus operates.

2. The extracorporeal blood treatment apparatus according to claim 1, wherein, as part of the integrity test procedure, the controller is configured to:
during said step of filling the first chamber of the ultrafilter with air, achieved by at least opening the air valve or operating the air pump operative on the air inlet line, also operating the waste pump based on a first set negative pressure value (P1) which is a desired set value to be reached by pressure sensed by the at least one pressure sensor; and
after said step of filling the first chamber of the ultrafilter with air, once the first chamber has been emptied from liquid and filled with air, operating the waste pump based on a second set negative pressure value (P2) which is a desired set value to be reached by pressure sensed by the at least one pressure sensor and which is more negative than the first pressure value,
wherein the set negative pressure threshold (Pt), which is checked during said verifying step, has a negative value intermediate between said first set pressure value (P1) and said second set pressure value (P2),
wherein the first set pressure value (P1) is selected in a pressure range between −150 mmHg and −450 mmHg, and
wherein the second set pressure value (P2) is selected in a pressure range between −300 mmHg and −700 mmHg, with the condition that the second pressure value be at least 100 mmHg more negative than the first set pressure value.

3. The extracorporeal blood treatment apparatus according to claim 1, wherein the supply line and the waste line are part of a hydraulic circuit configurable according to:
a normal configuration, wherein the outlet end of the supply line communicates with the inlet end of the waste line through the blood treatment device, and
a by-pass configuration, wherein the supply line is in fluid communication with the waste line via a by-pass line, and
wherein the hydraulic circuit is in the by-pass configuration during the integrity test procedure.

4. The extracorporeal blood treatment apparatus according to claim 1, wherein a fresh fluid pump is positioned on:
the air inlet line, or
the first tract of the supply line, between the air injection point and the first port of the ultrafilter,
wherein the controller is in communication with the fresh fluid pump and is configured to operate the fresh fluid pump during said filling of the first chamber of the ultrafilter with air, and
wherein the controller is in communication with the air valve, and wherein the controller is configured to cause the air valve to open with a delay from a start of the operation of the fresh fluid pump.

5. The extracorporeal blood treatment apparatus according to claim 4, comprising a safety pressure sensor located between the fresh fluid pump and the first chamber of the ultrafilter, and wherein the controller is configured to stop operation of the fresh fluid pump if a pressure difference or pressure ratio between pressure detected by pressure sensor and pressure detected by safety pressure sensor exceeds an identified safety threshold.

6. The extracorporeal blood treatment apparatus according to claim 1, wherein, as part of the integrity test procedure, the controller is further configured to:
hydraulically isolate the ultrafilter;
receive pressure values detected by the at least one pressure sensor at the end of a given transitory period after having hydraulically isolated the ultrafilter;
determine if either of two stability conditions are met, the stability conditions including:
whether pressure values detected by the at least one pressure sensor at the end of the transitory period are below an auxiliary negative pressure threshold (Pt2), or
whether a variation by unit of time (dP/dt) of said pressure values detected by the at least one pressure sensor at the end of the transitory period is below a set pressure differential (ΔP); and
determine that the semipermeable membrane of the ultrafilter has a multi-fiber break if said two stability conditions are not both met.

7. The extracorporeal blood treatment apparatus according to claim 1, wherein, as part of the integrity test procedure and after the controller has executed the steps of claim 1, the controller is further configured to:
hydraulically isolate the ultrafilter;
receive pressure values detected by the at least one pressure sensor at the end of a given transitory period after having hydraulically isolated the ultrafilter;
verify if either of two stability conditions are met:
pressure values detected by the at least one pressure sensor at the end of the transitory period are below an auxiliary negative pressure threshold (Pt2), and
a variation by unit of time (dP/dt) of said pressure values detected by the at least one pressure sensor at the end of the transitory period is below a set pressure differential (ΔP); and
determine that the semipermeable membrane of the ultrafilter has a multi-fiber break if said two stability conditions are not both met.

8. The extracorporeal blood treatment apparatus according to claim 1, wherein, as part of the integrity test procedure, the controller is further configured to:
hydraulically isolate the ultrafilter;
receive pressure values detected by the at least one pressure sensor during a further test interval after said transitory period, or a further transitory period, following hydraulic isolation of the ultrafilter;
verify if a variation by unit of time (dP/dt) of said pressure values detected by the at least one pressure sensor during the further test interval remains below a further set pressure differential (Δp2) for at least a portion of said test interval; and
    determine that the semipermeable membrane of the ultrafilter has a single-fiber break if the above last verifying step is not positively passed.
  9. The extracorporeal blood treatment apparatus according to claim 1, wherein, as part of the integrity test procedure and after the controller has executed the steps of claim 1, the controller is further configured to:
    hydraulically isolate the ultrafilter;
    receive pressure values detected by the at least one pressure sensor during a further test interval after a/said transitory period following hydraulic isolation of the ultrafilter;
    verify if a variation by unit of time (dP/dt) of said pressure values detected by the at least one pressure sensor during the further test interval remains below a further set pressure differential (Δp2) for at least a portion of said test interval; and
    determine that the semipermeable membrane of the ultrafilter has a single-fiber break if the above last verifying step is not positively passed.
  10. The extracorporeal blood treatment apparatus according to claim 1, comprising at least one of the air valve or the air pump located on the air inlet line and operatively connected to the controller, and wherein the step of causing filling of the first chamber of the ultrafilter with air is achieved by the controller by executing at least one of commanding opening of the air valve or commanding operation of the air pump.
  11. The extracorporeal blood treatment apparatus according to claim 6, comprising:
    at least one inlet valve on the supply line to selectively open and close supply of liquid from the source of treatment liquid;
    at least one outlet valve on the waste line to selectively open and close flow of used treatment liquid to the discharge;
    a flush line connecting a third port of the first chamber of the ultrafilter to the waste line; and
    at least one flush valve positioned on the flush line to selectively open and close the first chamber of the ultrafilter to the waste line,
    wherein, as part of the step of hydraulically isolating the ultrafilter, the controller is configured to:
      close at least said at least one inlet valve, at least one outlet valve, at least one flush valve and, optionally, the air valve, and
      stop the waste pump.
  12. The extracorporeal blood treatment apparatus according to claim 7, comprising:
    at least one inlet valve on the supply line to selectively open and close supply of liquid from the source of treatment liquid;
    at least one outlet valve on the waste line to selectively open and close flow of used treatment liquid to the discharge;
    a flush line connecting a third port of the first chamber of the ultrafilter to the waste line; and
    at least one flush valve positioned on the flush line to selectively open and close the first chamber of the ultrafilter to the waste line,
    wherein, as part of the step of hydraulically isolating the ultrafilter, the controller is configured to:
      close at least said at least one inlet valve, at least one outlet valve, at least one flush valve and, optionally, the air valve, and
      stop the waste pump.
  13. The extracorporeal blood treatment apparatus according to claim 6, comprising:
    at least one inlet valve on the supply line to selectively open and close supply of liquid from the source of treatment liquid;
    at least one outlet valve on the waste line to selectively open and close flow of used treatment liquid to the discharge;
    a flush line connecting a third port of the first chamber of the ultrafilter to the waste line; and
    at least one flush valve positioned on the flush line to selectively open and close the first chamber of the ultrafilter to the waste line,
    wherein, as part of the step of hydraulically isolating the ultrafilter, the controller is configured to:
      close at least said at least one inlet valve, at least one outlet valve, at least one flush valve and optionally the air inlet valve,
      stop the waste pump, and
      stop the fresh fluid pump.
  14. The extracorporeal blood treatment apparatus according to claim 7, comprising:
    at least one inlet valve on the supply line to selectively open and close supply of liquid from the source of treatment liquid;
    at least one outlet valve on the waste line to selectively open and close flow of used treatment liquid to the discharge;
    a flush line connecting a third port of the first chamber of the ultrafilter to the waste line; and
    at least one flush valve positioned on the flush line to selectively open and close the first chamber of the ultrafilter to the waste line,
    wherein, as part of the step of hydraulically isolating the ultrafilter, the controller is configured to:
      close at least said at least one inlet valve, at least one outlet valve, at least one flush valve and optionally the air inlet valve,
      stop the waste pump, and
      stop the fresh fluid pump.
  15. The extracorporeal blood treatment apparatus according to claim 1, comprising an auxiliary ultrafilter inserted in the second tract of the supply line and including a semipermeable membrane dividing the auxiliary ultrafilter into a respective first chamber and a respective second chamber, the auxiliary ultrafilter including:
    a first port connecting a first portion of the second tract of the supply line to the first chamber of the auxiliary ultrafilter;
    a second port connecting the second chamber of the auxiliary ultrafilter to a second portion of the second tract of the supply line;
    an auxiliary air inlet line connected to the first chamber of the auxiliary ultrafilter or to the first portion of the second tract of the supply line; and
    an auxiliary air valve or an auxiliary air pump on the air inlet line,
    wherein the at least one pressure sensor is configured to detect a pressure in one of:
      the second chamber of the auxiliary ultrafilter,
      the second portion of the second tract of the supply line, and
      the waste line, and wherein the supply line and the waste line are part of a hydraulic circuit configurable according to:
a normal configuration, wherein the outlet end of the supply line communicates with the inlet end of the waste line through the blood treatment device, and
a by-pass configuration, wherein the supply line is in fluid communication with the waste line via a by-pass line, and
wherein, with the supply line and the waste line in by-pass configuration and as part of the auxiliary integrity test procedure, the controller is configured to:
cause filling of the first chamber of the auxiliary ultrafilter with air by operating the waste pump,
after filling the first chamber of the auxiliary ultrafilter with air, increase a negative pressure in the second chamber of the auxiliary ultrafilter by continuing to operate the waste pump, pressure values being relative to atmospheric pressure present in the ambient where the apparatus operates,
verify, while the waste pump is running, if the pressure sensed by the at least one pressure sensor reaches a set negative pressure threshold (Pt'), and
determine that the auxiliary ultrafilter semipermeable membrane has a multi-fiber break if the pressure sensed by the at least one pressure sensor during said verification step does not reach said set negative pressure threshold (Pt') within an auxiliary set time interval (T').

16. The extracorporeal blood treatment apparatus according to claim 15, wherein the auxiliary air inlet line includes at least one of an auxiliary air valve and an auxiliary air pump and causing filling of the first chamber of the auxiliary ultrafilter includes the controller being configured to at least one of open the auxiliary air valve and operate the auxiliary air pump, and
wherein, as part of the auxiliary integrity test procedure, to operate the waste pump in a closed-loop the controller is configured to:
during said step of filling the first chamber of the auxiliary ultrafilter with air, control operation of the waste pump based on a first set negative pressure value (P1'), which is reached by pressure sensed by the at least one pressure sensor,
after said step of filling the first chamber of the auxiliary ultrafilter, once the first chamber has been completely emptied from liquid and filled with air, control operation of the waste pump based on a second set negative pressure value (P2'), which is reached by pressure sensed by the at least one pressure sensor and which is more negative than the first pressure value, and wherein the set negative pressure threshold (Pt') has a negative value intermediate between said first set pressure value (P1') and said second set pressure value (P2').

17. The extracorporeal blood treatment apparatus according to claim 16, wherein:
the first set pressure value (P1') is selected in a pressure range between −150 mmHg and −450 mmHg,
the second set pressure value (P2') is selected in the range between −300 mmHg and −700 mmHg, with the condition that the second pressure value be at least 100 mmHg more negative than the first set pressure value, and
the set negative pressure threshold (Pt') is selected to have a value which is intermediate between the first and second pressure values (P1', P2').

18. The extracorporeal blood treatment apparatus according to claim 11, wherein the controller is configured to:
detect a time related parameter, which is one of:
a time necessary to reach the first pressure value (P1'),
a rotation frequency of the waste pump, or
a pump rotation period of the waste pump; and
compare the detected time related parameter with a corresponding reference threshold, assigning the identification of a multi-fiber break problem in membrane of ultrafilter if the check on the time related parameter is not passed.

19. The extracorporeal blood treatment apparatus according to claim 12, wherein the controller is configured to:
detect a time related parameter, which is one of:
a time necessary to reach the first pressure value (P1'),
a rotation frequency of the waste pump, or
a pump rotation period of the waste pump; and
compare the detected time related parameter with a corresponding reference threshold, assigning the identification of a multi-fiber break problem in membrane of ultrafilter if the check on the time related parameter is not passed.

20. The extracorporeal blood treatment apparatus according to claim 15, wherein, as part of the auxiliary integrity test procedure, the controller is configured to:
hydraulically isolate the auxiliary ultrafilter;
receive pressure values detected by the at least one pressure sensor at the end of a given transitory period after having hydraulically isolated the auxiliary ultrafilter;
determine if either of two stability conditions are met, the stability conditions including:
whether pressure values detected by the at least one pressure sensor at the end of the transitory period are below an auxiliary negative pressure threshold, for example below −350 mmHg, and
whether a variation by unit of time (dP/dt) of said pressure values detected by the at least one pressure sensor at the end of the transitory period is below a set pressure differential, for example below 4 mmHg/s, optionally wherein the variation by unit of time (dP/dt) is determined by assigning a respective weight to each received pressure value, with the pressure values received during an initial phase of detection having more weight than pressure values received during an ending phase of detection; and
determine that the semipermeable membrane of the auxiliary ultrafilter has a multi-fiber break if said two stability conditions are not both met.

21. The extracorporeal blood treatment apparatus according to claim 15, wherein, as part of the auxiliary integrity test procedure, the controller is further configured to:
hydraulically isolate the auxiliary ultrafilter;
receive pressure values detected by the at least one pressure sensor during a further test interval subsequent to the transitory period following hydraulic isolation of the auxiliary ultrafilter;
verify if a variation by unit of time (dP/dt) of said pressure values detected by the at least one pressure sensor during the further test interval remains below a further set pressure differential (Δp2'); and
determine that the semipermeable membrane of the ultrafilter has a single-fiber break if the above last verifying step is not positively passed.

* * * * *